United States Patent [19]

Gall et al.

[11] Patent Number: 4,996,318
[45] Date of Patent: Feb. 26, 1991

[54] AMINO-9,10-SECOSTEROIDS USEFUL FOR TREATING HEAD INJURY, SPINAL CORD TRAUMA OR STROKE

[75] Inventors: Martin Gall, Kalamazoo, Mich.; Robert I. Higuchi, Palo Alto, Calif.

[73] Assignee: The Upjohn Company, Kalamazoo, Mich.

[21] Appl. No.: 438,480

[22] PCT Filed: Mar. 18, 1988

[86] PCT No.: PCT/US88/00817
  § 371 Date: Sep. 19, 1989
  § 102(e) Date: Sep. 19, 1989

[87] PCT Pub. No.: WO88/07527
  PCT Pub. Date: Oct. 6, 1988

[51] Int. Cl.$^5$ .............. C07D 405/00; C07D 403/00; C07D 279/12; C07D 413/00; C07D 253/00; C07D 239/02; C07D 241/00; C07D 241/02; C07D 413/00; C07D 277/04; C07D 209/04; C07C 221/00

[52] U.S. Cl. .............. 544/295; 540/450; 540/596; 540/597; 540/598; 540/601; 544/59; 544/60; 544/82; 544/111; 544/129; 544/130; 544/182; 544/211; 544/212; 544/217; 544/219; 544/309; 544/310; 544/311; 544/312; 544/313; 544/314; 544/331; 544/332; 544/336; 544/357; 544/360; 544/364; 544/405; 546/194; 546/268; 546/275; 546/276; 546/280; 546/281; 546/306; 546/312; 546/345; 548/100; 548/190; 548/194; 548/195; 548/325; 548/333; 548/336; 548/337; 548/469; 549/57; 564/180; 564/342; 564/345

[58] Field of Search .............. 564/180, 342, 345; 540/596, 597, 598, 601; 544/59, 60, 111, 129, 130, 182, 217, 219, 309, 310, 82, 311, 312, 313, 314, 295, 331, 332, 336, 357, 405, 211, 212, 360, 364; 546/194, 268, 275, 276, 280, 281, 306, 312, 345; 548/100, 190, 194, 195, 325, 333, 336, 337, 469; 549/57

[56] References Cited

U.S. PATENT DOCUMENTS 2,920,999 1/1960 Agnello .............. 167/65

FOREIGN PATENT DOCUMENTS

87/01706 3/1987 World Int. Prop. O. .

OTHER PUBLICATIONS

Oh-kita et al., Chem. Abst., 105-115530b, abst. of WO86/01797.
J. Chem. Soc. Chem. Commun., 709, (1982).
J. Chem. Soc. Chem. Commun., 1096, (1983).
Tetrahedron 2:80, (1958).

Primary Examiner—Cecilia Shen
Attorney, Agent, or Firm—Bruce Stein

[57] ABSTRACT

The amino-9,10-secosteroids

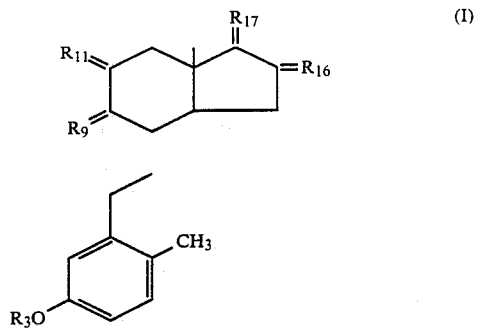

of the present invention contain an amino group attached to the terminal carbon atom of the $C_{17}$-side chain and are useful as pharmaceutical agents for treating a number of conditions including spinal trauma, mild and/or moderate to severe head injury, etc.

18 Claims, No Drawings

AMINO-9,10-SECOSTEROIDS USEFUL FOR TREATING HEAD INJURY, SPINAL CORD TRAUMA OR STROKE

BACKGROUND OF THE INVENTION

1. Field of the Invention

Disclosed are 9,10-secosteroids substituted at $C_{17}$ with a substituent which has an amino group. These compounds are useful pharmaceutical agents in treating head injury, spinal cord trauma or stroke.

2. Description of the Related Art

Secosteroids are well known to those skilled in the art, see J. Chem. Soc. Chem. Commun., 709 (1982), ibid 1096 (1983) and Tetrahedron 2, 80 (1958). However, none of the prior art secosteroids contain an amine functionality at the $C_{terminal}$ position of the $C_{17}$ side chain. Further, none of these secosteroids is useful in treating, head injury, spinal cord trauma or stroke.

Published PCT patent application Ser. No. 86/01797 discloses amino steroids where the amine portion includes acyclic, aromatic and heterocyclic amine functionality very similar to the amino substituents of the present invention. In published PCT patent application Ser. No. 86/01797, the amino substituent was attached to the terminal carbon atom of the steroidal $C_{17}$ side chain. The present invention differs from Published PCT patent application Ser. No. 86/01797 in that the non-amine portion is not a steroid. Published PCT patent application Ser. NO. 86/01797 also disclosed numerous references involving various amines and amino substituents which are incorporated here by reference. Published PCT patent application Ser. No. 86/01797 is the reference which discloses amino substituents most similar to those of the present invention.

German Patent No. 1,087,598 and U.S. Pat. No. 2,920,999 disclose simple 21-amino derivatives of $\Delta^4$-3-keto steroids. The amines include both mono and bis substituted amines. In the cases where the amino group is disubstituted, the two substituents can be cyclized with the attached nitrogen atom to form a heterocyclic amino group (morpholine, pyrrolidine, piperidine, pyridine). The amines were chosen from the group consisting of amino, monoalkylamino, dialkylamino, phenylamino, pyridylamino, benzylamino, picolinylamino, N-alkyl-N-phenylamino, N-alkyl-N-pyridylamino, morpholinyl, pyrryl, pyrrolidyl, piperidino and C-alkylated piperidino, though only N-piperidino, N,N-diethyl and N-methyl-N-phenyl were exemplified.

SUMMARY OF INVENTION

Disclosed is an amino-9,10-secosteroid of formula (I) where:

$R_3$ is —H or —CO-$R_{3-1}$ is $C_1$-$C_4$ alkyl or phenyl optionally substituted with 1 or 2 $R_{3-2}$ where $R_{3-2}$ is —CH$_3$, —OCH$_3$, —F and —Cl;

(C-I) $R_9$ is $R_{9-1}$:$R_{9-2}$ and $R_{11}$ is $R_{11-1}$:$R_{11-2}$, where one of $R_{9-1}$ and $R_{9-2}$ is —H and the other taken together with one of $R_{11-1}$ and $R_{11-2}$ to form a second bond between $C_9$ and $C_{11}$ and the other of $R_{11-1}$ and $R_{11-2}$ is —H;

(C-II) $R_9$ is —H:—H and $R_{11}$ is =O;

(C-III) $R_9$ is —H:—H and $R_{11}$ is $\alpha$-$R_{11-3}$:$\beta$-$R_{11-4}$ where one of $R_{11-3}$ and $R_{11-4}$ is —H or —OH and the other is —H;

(D-I) $R_{16}$ is $R_{16-1}$:$R_{16-2}$ and $R_{17}$ is $R_{17-1}$:$R_{17-2}$, where one of $R_{16-1}$ and $R_{16-2}$ is —H or —CH$_3$ and the other taken together with one of $R_{17-1}$ and $R_{17-2}$ forms a second bond between $C_{16}$ and $C_{17}$, and the other of $R_{17-1}$ and $R_{17-2}$ is —C(=Z)—(CH$_2$)$_n$—NR$_{21A}$R$_{21B}$, where Z is =O, =CH$_2$ or $R_{20-1}$:—H where $R_{20-1}$ is —H or —CH$_3$, where n is 0 through 6, where (A) $R_{21A}$ is (1) —(CH$_2$)$_m$—NR$_{21-1}$-heteroaryl, where m is 2, 3 or 4, where $R_{21-1}$ is —H or $C_1$-$C_3$ alkyl, where heteroaryl is:

(a) pyridin-2- (F-1), 3- (R-2) or 4-yl (F-3) or the N-oxide thereof optionally substituted by 1 or 2 $R_{21-2}$, being the same or different, where $R_{21-2}$ is (i) —F,
(ii) —Cl,
(iii) —Br,
(iv) $C_1$-$C_5$ alkyl,
(v) —CH$_2$—CH=CH$_2$,
(vi) -13 aryl, where aryl is phenyl optionally substituted with 1 through 2 —F, —Cl, —Br, $C_1$-$C_3$ alkoxy, —COOH, —NH$_2$, $C_1$-$C_3$ alkylamino, di($C_1$-$C_3$)alkylamino, where the alkyl groups are the same or different, 1-pyrrolidinyl-, 1-piperidinyl, 1-hexamethylenimino-, 1-heptamethylenimino-, $C_2$-$C_4$ acylamino and —NH—CHO;
(vii) -NR$_{21-3}$R$_{21-3}$ where the $R_{21-3}$s are the same or different and are —H, $C_1$-$C_3$ alkyl or —CH$_2$—CH=CH$_2$,
(viii$\alpha$) *CH$_2$—(CH$_2$)$_q$—CH$_2$—N*— where the atoms marked with an asterisk (*) are bonded to each other resulting in the formation of a ring, where q is 1 through 5,
(viii$\beta$) *CH$_2$—CH$_2$—(CH$_2$)$_c$—G—(CH$_2$)$_d$—CH$_2$—CH$_2$—N*—where the atoms marked with an asterisk (*) are bonded to each other resulting in the formation of a ring (F—4), where G is —O—, —S—, —SO—, —SO$_2$— or —NHR$_{21-4}$, where $R_{21-4}$ is —H, $C_1$-$C_3$ alkyl, or aryl as defined above, where c and d are the same or different and are 0 through 2 with the proviso that the total number of ring carbon atoms is 4, 5 or 6,
(ix) 3-pyrrolin-1-yl, (F-5)
(x) pyrrol-1-yl optionally substituted with $C_1$-$C_3$ alkyl, (F-6)
(xi) piperidin-1-yl optionally substituted with 1 or 2 $C_1$-$C_3$ alkyl, (F-7)
(xii) 1,2,3,6-tetrahydropyridin-1-yl, (F-8)
(xiii) 1-hexamethyleneimino containing a 3-or 4-double bond or 3- and 5-double bonds, (F-9)
(xiv) 1,4-dihydro-1-pyridinyl substituted in the 4 position by two $C_1$-$C_3$ alkyl being the same or different, (F-10)
(xv) —OH,
(xvi) $C_1$-$C_3$ alkoxy,
(xvii) —NR$_{21-7}$—(CH$_2$)$_e$—Q where Q is 2-pyridinyl where $R_{21-7}$ is —H or $C_1$-$C_3$ alkyl and e is 0 through 3,
(xviii) pyridin-2-, 3- or 4-yl,
(xix) —CF$_3$
(xx) —CCl$_3$ (b) 1,3,5-triazin-2-yl or the N-oxide thereof optionally substituted at the 4- and/or 6- position with $R_{21-2}$ where $R_{21-2}$ is as defined above, (F-11)

(c) pyrimidin-4-yl or the N-oxide thereof optionally substituted at the 2- and/or 6- and 5- and/or 6- position with $R_{21-2}$ where $R_{21-2}$ is as defined above, (F-12)

(d) pyrimidin-2-yl optionally substituted at 4- and/or 6- position with 1 or 2 $R_{21-2}$ as is defined above, (F-13

(e) pyrazin-2-yl optionally substituted with 1 or 2 $R_{21-2}$ as is defined above, (F-14)

(f) imidazol-2-yl optionally substituted in the 1 position with $C_1$-$C_3$ alkyl or -aryl, where aryl is as defined above, and further optionally substituted with 1 or 2 $R_{21-2}$ as defined above, (F-15)

(g) 1,3,4-triazol-2-yl optionally substituted in the 1 position with $C_1$-$C_3$ alkyl or -aryl, where aryl is as defined above, and further optionally substituted with $R_{21-2}$ as defined above, (F-16)

(h) imidazol-4- or 5-yl optionally substituted in the 1 position with $C_1$-$C_3$ alkyl or -aryl, where aryl is as defined above, and further optionally substituted with 1 or 2 $R_{21-2}$ as defined above, (F-17)

(i) benzo[b]thien-2-yl, (F-18)

(j) indol-2-yl, (F-19)

(k) benzo[b]thiazol-2-yl, (F-20)

(l) benzimidazol-2-yl, (F-21)

(m) 4-[2-[4-[2,6-bis(1-pyrrolidinyl)-4-pyrimidinyl]-1-piperazinyl]ethyl]piperazinyl, (F-22)

(n) 1,2,4-triazin-3-yl optionally substituted at the 5- and/or 6- position with $R_{21-2}$ is as defined above, (F-23)

(2) (1-piperazinyl)-($C_2$-$C_4$) alkyl optionally substituted in the 4- position with -aryl or -heteroaryl as defined above, (F-24)

(3) -heteroaryl, as defined above, (4) —$(CH_2)_m$—$X_4$ where m is as defined above and where $X_4$ is (a) —O—$CH_2CH_2$-Y, where Y is $C_1$-$C_3$ alkyl-amino, di($C_1$-$C_3$)alkylamino where the alkyl groups are the same or different, $C_3$-$C_6$ alkyleneimino, optionally substituted with 1 or 2 $C_1$-$C_3$ alkyl, (b) —$NR_{21-5}CH_2CH_2$—Y, where $R_{21-5}$ is —H or $C_1$-$C_3$ alkyl and Y is as defined above, (c) —$(CH_2)_g$—$N(R_{21-5})$—heteroaryl, where g is 2, 3 or 4, and where $R_{21-5}$ and heteroaryl are as defined above, (6) —$(CHCH_3)_b$-$(CH_2)_f$—$R_{21-9}$, where b is 0 and f is 1 through 3 or b is one and f is 0 through 3, where $R_{21-9}$ is phenyl substituted with 1 through 3 —OH, $C_1$-$C_3$ alkoxy, —$NR_{21-10}R_{21-11}$ where $R_{21-10}$ and $R_{21-11}$ are the same or different and are —H, $C_1$-$C_3$ alkyl or are taken together with the attached nitrogen atom to form a $C_4$-$C_7$ cyclicamino ring, (7) —$(CH_2)_i$—heteroaryl, where i is 1 through 4 and heteroaryl is as defined above, (8) (1piperazinyl)acetyl substituted in the 4-position by heteroaryl where heteroaryl is as defined above, (F-25)

(9) (1-piperazinyl)carbonylmethyl substituted in the 4-position by -heteroaryl where heteroaryl is as defined above, and (F-26)

(B) $R_{21B}$ is (1) —H, (2) $C_1$-$C_3$ alkyl, (3) $C_5$-$C_7$ cycloalkyl, (4) —$(CH_2)_m$—$NR_{21-1}$-heteroaryl, where m, $R_{21-1}$ and heteroaryl are as defined above, (5) (1-piperazinyl)-($C_2$-$C_4$)alkyl optionally substituted in the 4- position with -aryl or -heteroaryl as defined above, (F-24)

(6) -13 $(CH_2)_m$—$X_4$, where m and $X_4$ are as defined above, (7) —$(CH_2)_m$—$NR_{21-6}R_{21-8}$, where m, $R_{21-6}$ and $R_{21-8}$ are as defined above, (8) -13 $(CHCH_3)_b$—$(CH_2)_f$—$R_{21-9}$, where b, f and $R_{21-9}$ are as defined above, (C) $R_{21A}$ and $R_{21B}$ are taken together with the attached nitrogen atom to form a heterocyclic ring selected from the group consisting of (1) 2-(carboxy)-1-pyrrolidinyl optionally as the $C_1$-$C_3$ alkyl ester or as a pharmaceutically acceptable salt, (F-27)

(2) 2-(carboxy)-1-piperidinyl optionally as the $C_1$-$C_3$ alkyl ester or as a pharmaceutically acceptable salt, (F-28)

(3) 2-(carboxy)-1-hexamethyleneimino optionally as the $C_1$-$C_3$ alkyl ester or as a pharmaceutically acceptable salt, (F-29)

(4) 2-(carboxy)-1-heptamethyleneimino optionally as the $C_1$-$C_3$ alkyl ester or as a pharmaceutically acceptable salt, (F-30)

(5) 1-piperazinyl substituted in the 4- position with $R_{21-12}$—CO—$(CH_2)_j$— where $R_{21-12}$ is -heteroaryl, —$NR_{21-13}$ heteroaryl and 2-furanyl, where $R_{21-13}$ is -H or $C_1$-$C_3$ alkyl, where j is 0 through 3 and aryl is as defined above, (F-31)

(6) 1-piperazinyl substituted in the 4- position with heteroaryl-$(CH_2)_j$—, where heteroaryl and j are as defined above, (F-32)

(7) 1-piperazinyl substituted in the 4- position with aryl-$(CH_2)_j$—, where aryl and j are as defined above, (F-33)

(8) 4-hydroxy-1-piperidinyl substituted in the 4-position with aryl as defined above, (F-34)

(9) 1-piperazinyl substituted in the 4- position with heteroaryl—$NR_{21-13}$—CO—$(CH_2)_i$—, where heteroaryl, $R_{21-13}$ and i are as defined above; (F-35)

(D-II) $R_{16}$ is $\alpha$-$R_{16-3}$:$\beta$-$R_{16-4}$ where one of $R_{16-3}$ and $R_{16-4}$ is —H and the other is —H, —F, —$CH_3$ or —OH, and $R_{17}$ is =CH—$(CH_2)_p$—$NR_{21A}$—$R_{21B}$, where p is 1 or 2, where $R_{21A}$ and $R_{21B}$ are as defined above;

(D-III) $R_{16}$ is $\alpha$-$R_{16-5}$:$\beta$-$R_{16-6}$ and $R_{17}$ is $\alpha$-$R_{17-5}$:$\beta$-$R_{17-6}$, where $R_{16-5}$ is —H, —OH, —F or -13 $CH_3$ and $R_{16-6}$ is —H, —OH, —F, or —$CH_3$, with the proviso that at least one of $R_{16-5}$ and $R_{16-6}$ is —H, where $R_{17-5}$ is —H, —OH, —$CH_2CH_3$, $C_2$-$C_7$ alkanoyloxy or —O—CO—aryl, where aryl is as defined above, and $R_{17-6}$ is —$C(=Z)$—$(CH_2)_n$—$NR_{21A}R_{21B}$, where Z, n, $R_{21A}$ and $R_{21B}$ are as defined above;

(D-IV) the 16, 17-acetonide of a compound where $R_{16-5}$ is —OH, $R_{16-6}$ is —H, $R_{17-5}$ is —OH and $R_{17-6}$ is —$C(=Z)$—$(CH_2)_n$—$NR_{21A}R_{21B}$, where Z, n, —$R_{21A}$ and $R_{21B}$ are as defined above;

(D-V) $R_{16}$ is $\alpha$-$R_{16-7}$:$\beta$-$R_{16-8}$ and $R_{17}$ is $\alpha$-$C(=Z)$—$(CH_2)_n$—N—$R_{21A}R_{21B}$:$\beta$-H where Z, n, $R_{21A}$ and $R_{21B}$ are as defined above, where $R_{16-7}$ is —H, —OH, —F or —$CH_3$ and $R_{16-8}$ is —H, —OH, —F, or —$CH_3$, with the proviso that at least one of $R_{16-5}$ and $R_{16-6}$ is —H and pharmaceutically acceptable salts thereof, and hydrates and solvates thereof.

Further disclosed are amino-9,10-secosteroids (I) where $R_{16}$ and $R_{17}$ are (D-II) $R_{16}$ is $\alpha$-$R_{16-3}$:$\beta$-$R_{16-4}$ where one of $R_{16-3}$ and $R_{16-4}$ is —H and the other is —H, —F, —$CH_3$ or —OH, and $R_{17}$ is =CH—$(CH_2)_p$—$NR_{21A}R_{21B}$;

(D-III) $R_{16}$ is $\alpha$-$R_{16-5}$:$\beta$-$R_{16-6}$ and $R_{17}$ is $\alpha$-$R_{17-5}$:$\beta$-$R_{17-6}$, where $R_{16-5}$ is —H, —OH, —F or —$CH_3$ and $R_{16-6}$ is —H, —OH, —F, or —$CH_3$, with the proviso that at least one of $R_{16-5}$ and $R_{16-6}$ is —H, where $R_{17-5}$ is —H, —OH, —CH$_3$, —CH$_2$CH$_3$, $C_2$-$C_7$ alkanoyloxy or —O—CO—aryl, and where $R_{17-6}$ is —C(=Z)—(CH$_2$)$_n$—NR$_{21A}$R$_{21B}$;

(D-IV) the 16,17-acetonide of a compound where $R_{16-5}$ is —OH, $R_{16-6}$ is —H, $R_{17-5}$ is —OH and $R_{17-6}$ is —C(=Z)—(CH$_2$)$_n$—NR$_{21A}$R$_{21B}$;

(D-V) $R_{16}$ is $\alpha$-$R_{16-7}$:$\beta$-$R_{16-8}$ and $R_{17}$ is $\alpha$-C(=Z)—(CH$_2$)$_n$—N—R$_{21A}$R$_{21B}$:$\beta$-H where Z, n, $R_{21A}$ and $R_{21B}$ are as defined above, where $R_{16-7}$ is —H, —OH, —R or —CH$_3$ and $R_{16-8}$ is —H, —OH, —F, or —CH$_3$, with the proviso that at least one of $R_{16-5}$ and $R_{16-6}$ is —H.

Also disclosed are amino-9,10-secosteroids (I) where $R_{17}$ is $\alpha$-$R_{17-5}$:$\beta$-$R_{17-6}$, where $R_{17-5}$ is —H, —OH, —CH$_3$, —CH$_2$CH$_3$, $C_2$-$C_7$ alkanoyloxy or —O—CO—aryl, and where $R_{17-6}$ is —C(=Z)—(CH$_2$)$_n$NR$_{21A}$R$_{21B}$.

Additionally disclosed are amino-9,10-secosteroids (I) where $R_{17}$ is =CH—(CH$_2$)$_p$—NR$_{21A}$R$_B$.

Further disclosed are amino-9,10-secosteroids (I) where $R_{11}$ is =O.

Also disclosed are amino-9,10-secosteroids (I) where $R_9$ is $R_{9-1}$:$R_{9-2}$ and $R_{11}$ is $R_{11-1}$:$R_{11-2}$, where one of $R_{9-1}$ and $R_{9-2}$ is —H and the other taken together with one of $R_{11-1}$ and $R_{11-2}$ to form a second bond between $C_9$ and $C_{11}$ and the other of $R_{11-1}$ and $R_{11-2}$ is —H.

DETAILED DESCRIPTION OF THE INVENTION

The amino-9,10-secosteroids (I), also known as octahydro indenones or indenes, of the present invention can be thought of as being made of two parts, an amine portion and a secosteroid portion. The desired amino-9,10-secosteroids (I) are preferably prepared by condensing the desired amine portion with the desired secosteroid portion.

The preferred amino-9,10-secosteroids (I) have a keto functionality at what is $C_{11}$ of a steroid. Therefore, one either starts with a 11-keto steroid (corticoid or non-corticoid) or the corresponding 11$\alpha$- or 11$\beta$-hydroxy steroid, and oxidizes it to the corresponding 11-keto steroid by methods well known to those skilled in the art, preferably pyridinium chlorochromate/sodium acetate in a solvent such as methylene chloride; see, EXAMPLE 2. EXAMPLE 1 demonstrates one convenient method to protect the 17$\alpha$- and 21-hydroxy groups during the oxidation of the secondary alcohol at $C_{11}$.

The intact $\Delta^{1,4}$-3-keto steroid starting material is then converted to a secosteroid by methods well known to those skilled in the art, see for example J. Chem. Soc. Chem. Commun., 709 (1982), ibid 1096 (1983) and Tetrahedron 2, 80 (1958). Preferred is the process using lithium and ammonia in THF; see, EXAMPLE 3. The free hydroxyl groups of the $C_{17}$-side chain may be appropriately protected as determined and by procedures known to those skilled in the art. If a "$\Delta^{9(11)}$"-secosteroid is desired then it is preferable to use samarium iodide or n-tributyl tin hydride on the xanthate ester of an 11-hydroxy steroid.

Next, the hydroxyl group at the $C_5$ position of the secosteroid ($C_3$ of a steroid) is optionally protected by methods well known to those skilled in the art, for example as the benzyl ether; see, EXAMPLE 4.

Next, the protecting groups on the $C_{17}$ side chain are removed by methods well known to those skilled in the art appropriate for the particular protecting group. For example, if there are hydroxy groups at 17 and 21 of the corticoid type starting material, and they are protected as the acetonide, this group is readily removed by acid as is well known to those skilled in the art, see EXAMPLE 5. This is done so as to be able to functionalize the position to which the amine will attach with a good leaving group such as tosylate, mesylate, chloride, bromide, iodide, and equivalents thereof, see EXAMPLE 6.

Next what corresponds to the "21-position" of the parent steroid is converted from a hydroxy functionality to a good leaving group such as chloride and/or tosylate. The use of p-toluenesulfonyl chloride produces both the chloro and tosyl derivatives. This mixture can be separated if desired. However, since both react with the amines to produce the desired amino-9,10-secosteroids (I), it is preferred to react the mixture of chloro and tosyl derivatives. Alternatively and preferably the leaving group, when chloride, can be introduced by use of triphenylphosphine and carbon tetrachloride, see EXAMPLE 15.

The desired secosteroid with a good leaving group in the position to which it is desired to attach the amine, and the desired amine are condensed in an aprotic solvent such as acetonitrile, DMF, THF, methylene chloride, DMA, ether and the like containing a base. It is preferred that the solvent be DMF or if a mixture, contain a high % of DMF. It is further preferred that the condensation take place in the presence of an iodide, such as sodium or potassium. Suitable bases include carbonate, bicarbonate, triethylamine, diisopropylethylamine and the like.

Last, any remaining protecting groups removable by hydrogenolysis are removed by methods well known to those skilled in the art; see EXAMPLES 8, 10 and 12 to produce the desired amino-9,10-secosteroid (I). Alternatively, cyclohexadiene can be used in place of cyclohexene.

If it is desired that $R_{11}$ be $\alpha$-H:$\beta$-OH or $\alpha$-OH:$\beta$-H, the compound where $R_{11}$ is =O is reduced with sodium borohydride or lithium selectride. Further, if it is desired that there be a double bond in the position $C_9$ to $C_{11}$ of the parent steroid (one of $R_{9-1}$ or $R_{9-2}$ are taken together with one of $R_{11-1}$ and $R_{11-2}$ to form a second bond between $C_9$ and $C_{11}$) the 11-hydroxy form is dehydrated by means well known to those skilled in the art or preferably one forms the $\Delta^{9(11)}$ double bond when one transforms the steroid to the secosteroid by the process disclosed in J. Chem. Soc. Chem. Commun., 709 (1982).

If it is desired that the substituent at $C_{17\alpha}$ be —H rather than —OH, the hydroxyl group can be removed by reaction with TMS-I (trimethylsilyl iodide). This can be done before or after the steroid is converted to the secosteroid, preferably before.

It is preferred that the condensation of the amine and secosteroid be the desired amine and desired secosteroid with the exception of readily removable protecting groups. Alternatively, in principle, a (derivative) form of the secosteroid not necessarily desired as the final product (I), can be reacted in its $C_{terminal}$ 21-halo, 21mesylate or 21-tosylate form with the appropriate amine to afford an amino-9,10-secosteroid. Following this, the secosteroid nucleus itself can be modified to produce the desired amino-9,10-secosteroid (I). While this is an alternative process, in principle, to produce the amino-9,10-secosteroids (I) of the present invention, in practice it is an undesirable method compared to the preferred process of reacting the $C_{terminal}$ halo, tosyl or mesyl analog corresponding to the secosteroid portion of desired amino-9,10-secosteroids (I), with an amine corresponding to the amine portion of the desired amino-9,10-secosteroids (I) as is apparent to one skilled in the art.

Yet another alternative procedure, in principle, to produce some of the amino-9,10-secosteroids (I) of the invention which involve amino substituents which can be thought of as having 2 or more components, can be produced by first reacting the halo, tosyl or mesyl secosteroid with a portion of the desired amine substituent to form an aminosecosteroid in which there is an amine substituent at the $C_{terminal}$-position followed by further reaction of the amino portion of the amino-9,10-secosteroid to produce the complete amine substituent at the $C_{terminal}$ position. While this is an alternative process in principle, in practice it is usually undesirable compared to the preferred process.

It is preferred that the $R_3$ group is —H, acetyl or benzyl. It is more preferred that $R_3$ be —H.

In what is known to those skilled in the art as the C-ring of a steroid, the substitution includes 11-keto, $\Delta^{9(11)}$, and 11-($\alpha/\beta$)-hydroxy. It is preferred that the substitution be 11-keto.

With the $\Delta^{16}$-9,10-secosteroid (I), it is preferred that the substituent at $C_{16}$ be —H. With the other 9,10-secosteroids (I) having two substituents at $C_{16}$, it is preferred that the substituent be either two —H's or a —H and a —CH$_3$. If —CH$_3$, it is preferred that it be in the $\alpha$ configuration.

It is preferred that the side chain at $C_{17}$ be —C(=Z)—(CH$_2$)$_n$—N—R$_{21A}$R$_{21B}$. It is preferred that Z is =O or —H,—H, it is more preferred that Z is =O. It is preferred that n is 1. It is preferred that R$_{21A}$ and R$_{21B}$ be taken together with the attached nitrogen atom to form a heterocyclic ring. It is preferred that the heterocyclic ring be 1-piperazinyl substituted in the 4- position with -(CH$_2$)$_j$-heteroaryl (F-32) or 1-piperazinyl substituted in the 4- position with -(CH$_2$)$_j$-aryl (F-33). It is more preferred that the heterocyclic ring be 1-piperazinyl substituted in the 4-position with -(CH$_2$)$_j$-heteroaryl. It is preferred that j is 0. With the substituent -(CH$_2$)$_j$-heteroaryl, it is preferred that heteroaryl be selected from the group consisting of 1,3,5-triazin-4-yl substituted in the 2- and/or 6- position with 2-pyridinyl, pyrimidin-4-yl substituted in the 2- and/or 6- position with 1-pyrrolidinyl, pyrimidin-4-yl substituted in the 2- and/or 6- position with 4-morpholinyl, 1,3,5-triazin-4-yl substituted in the 2- and 6- position with 1-pyrrolidinyl and pyridinyl substituted in the 3- position with —NR$_{21-3}$R$_{21-3}$ where one of R$_{21-3}$ is —H and the other is C$_2$ alkyl. It is preferred that the compounds not be the N-oxide. It is also preferred that heteroaryl be selected from the group consisting of
(a) 1,3,5-triazin-4-yl optionally substituted in the 2- and/or 6- position with R$_{21-2}$,
(b) pyrimidin-2-yl optionally substituted at 4- and/or 6- position with 1 or 2 R$_{21-2}$,
(c) pyrimidin-4-yl optionally substituted at the 2- and/or 6- position with R$_{21-2}$ and
(d) pyridin-2-yl optionally substituted by 1 or 2 R$_{21-2}$, being the same or different. It is further preferred that heteroaryl be selected from the group consisting of
(a) 1,3,5-triazin-4-yl substituted at the 2- and 6- position with pyrrolidine or diethylamine,
(b) pyrimidin-2-yl optionally substituted at the 4- and 6- position with pyrrolidine,
(c) pyrimidin-4-yl optionally substituted at the 2- and 6- position with pyrrolidine or diethylamine,
(d) pyridin-2-yl and
(e) pyridin-2-yl substituted with pyrrolidine, ethylamine or diethylamine.

It is preferred that the heterocyclic ring be selected from the group consisting of
4-(2-pyridinyl)-1-piperazinyl,
4-[4,6-bis(2-propenylamino)-1,3,5-triazin-2-yl]-1-piperazinyl,
4-[2,6-bis(1-pyrrolidinyl)-4-pyrimidinyl]-1-piperazinyl,
4-[2,6-bis(morpholino)-4-pyrimidinyl]-1-piperazinyl,
4-[4,6-bis(diethylamino)-2-pyrimidinyl]-1-piperazinyl,
4-[4,6-bis(1-pyrrolidinyl)-1,3,5-triazin-2-yl]-1-piperazinyl,
4-[3,6-bis(diethylamino)-2-pyridinyl]-1-piperazinyl,
4-[3-ethylamino)-2-pyridinyl]-1-piperazinyl,
4-[6-(diethylamino)-2-pyridinyl]-1-piperazinyl,
4-[4,6-bis(2-pyridinyl)-1,3,5-triazin-2-yl]-1-piperazinyl and
4-[2,6-bis(2-pyridinyl)-4-pyrimidinyl]-1-piperazinyl.

It is preferred that the amino-9,10-secosteroid (I) be selected from the group consisting of
3a-methyl-3$\alpha$-hydroxy-7-[2-(5-hydroxy-2-methylphenyl)-ethyl]-3-[2-[4-(2,6-bis(1-pyrrolidinyl)-4-pyrimidinyl)-1-piperazinyl]acetyl]octahydro-5H-inden-5-one,
3a-methyl-3$\alpha$-hydroxy-7-[2-(5-hydroxy-2-methylphenyl)-ethyl]-3-[2-[4-(2-pyridinyl)-1-piperazinyl]acetyl]octahydro-5H-inden-5-one,
3a-methyl-3$\alpha$-hydroxy-7-[2-(5-hydroxy-2-methylphenyl)-ethyl]-3- [2-[4-[3-(ethylamino)-2-pyridinyl]-1-piperazinyl]acetyl]-octahydro-5H-inden-5-one,
3a-methyl-7-[2-(5-hydroxy-2-methylphenyl)-ethyl]-3-[2-[4-(2,6-bis(1-pyrrolidinyl)-4-pyrimidinyl)-1-piperazinyl]ethyl]-3$\alpha$-octahydro-5H-inden-5-one,
3a-methyl-7-[2-(5-hydroxy-2-methylphenyl)-ethyl]-3-[2-[4-[3-(ethylamino)-2-pyridinyl]-1-piperazinyl]ethyl]-3$\alpha$-octahydro-5H-inden-5-one,
3a-Methyl-3$\alpha$-hydroxy-7-[2-(5-hydroxy-2-methylphenyl)-ethyl]-3-[2-[4-[2,6-bis(2-pyridinyl)-4-pyrimidinyl]-1-piperazinyl]acetyl]octahydro-5H-inden-5-one,
3a-methyl-7-[2-(5-hydroxy-2-methylphenyl)-ethyl]-3-[2-[4-[3-(ethylamino)-2-pyridinyl]-1-piperazinyl]ethylidene]-3$\alpha$-octahydro-5H-inden-5-one,
3a-methyl-7-[2-(5-hydroxy-2-methylphenyl)-ethyl]-3-[2-[4-[3-(ethylamino)-2-pyridinyl]-1-piperazinyl]acetyl]-3$\alpha$-octahydro-5H-inden-5-one,
3a-methyl-7-[2-(5-hydroxy-2-methylphenyl)-ethyl]-3-[2-[4-(2,6-bis(1-pyrrolidinyl)-4-pyrimidinyl)-1-piperazinyl]ethyl]-3$\alpha$-octahydro-5H-inden-5-one,
3a-methyl-7-[2-(5-hydroxy-2-methylphenyl)ethyl]-3$\alpha$-[2-[4-(4-(2,6-bis(1-pyrrolidinyl)-4-pyrimidinyl)-1-piperazinyl]acetyl]-3$\beta$-octahydro-5H-inden-5-one,
3a-methyl-7-[2-(5-hydroxy-2-methylphenyl)ethyl]-3$\alpha$-[2-[4-[3-(ethylamino)-2-pyridinyl]-1-piperazinyl]acetyl]-3$\beta$-octahydro-5H-inden-5-one,
3a-methyl-3$\beta$-[2-[4-[3,6-bis(diethylamino)-2-pyridinyl]-1-piperazinyl]acetyl]-7 -[2-(5-hydroxy-2-methylphenyl)ethyl]-3$\alpha$-octahydro-5H-inden-5-one,
7a-methyl-1$\beta$-[2-[4-[3-(ethylamino)-2-pyridinyl]-1-piperazinyl]acetyl]-4$\alpha$-[2-(5-hydroxy-2-methylphenyl)-ethyl]-2, 3, 3a$\alpha$, 4, 7, 7a-hexahydro-$\Delta^5$-1H-indene,
7a-methyl-4$\alpha$-[2-(5-hydroxy-2-methylphenyl)-ethyl]-1$\beta$-[2-[4-(2,6-bis(1-pyrrolidinyl)-4-pyrimidinyl)-1- piperazinyl]acetyl]-2, 3, 3aα, 4, 7, 7a-hexahydro-Δ⁵-1H-indene.

The amino-9,10-secosteroids (I) of the present invention are reacted with acids to form amine salts by methods known to those skilled in the art and the resulting salts are more water soluble and therefore preferable to use when an aqueous formulation is desired such as a solution for IV use. Generally the amino-9,10-secosteroids (I) possess one or more basic nitrogen atoms to be converted to an acid addition pharmaceutically acceptable salt. However, when n is 0 and Z is =O and the compound does not contain another nitrogen atom, they will not form salts suitable as pharmaceuticals. The pharmaceutically acceptable salt forms of the amino substituted steroids (I) are generally preferred over the free base form since the salts have greater water solubility and form crystals more suitable for pharmaceutical purposes. An acid addition salt of the amino-9,10-secosteroids (I) can be converted to the free base, which can be converted to any desired pharmaceutically acceptable acid addition salt by methods known to those skilled in the art. It is preferred that the acid addition salt be prepared by reacting the free base of the amino-9,10-secosteroids (I) with an approximately stoichiometric amount of an acid, such as hydrochloric, hydrobromic, hydroiodic, sulfuric, phosphoric, acetic, lactic, citric, succinic, benzoic, salicylic, pamoic, cyclohexanesulfamic, methanesulfonic, naphthalenesulfonic, p-toluenesulfonic, maleic, fumaric, oxalic acid and the like. It is preferred that the acid be selected from the group consisting of hydrochloric, maleic, methanesulfonic and fumaric acids.

The amino-9,10-secosteroids (I) and acid addition salts thereof can be isolated as hydrates or solvents, and such forms are regarded as equivalent to the corresponding amino-9,10-secosteroids (I) not containing water or solvent.

The amino-9,10-secosteroids (I) of the present invention are useful pharmaceutical agents in treating a number of different medical conditions in humans and useful warm blooded animals.

In humans, the amino-9,10-secosteroids (I) of the present invention are useful in treating spinal trauma, mild and/or moderate to severe head injury, subarachnoid hemorrhage and subsequent cerebral vasospasm, ischemic (thromboembolic) stroke, excess mucous secretion, asthma, muscular dystrophy, adriamycin-induced cardiac toxicity, adriamycin induced cytotoxicity during anti-cancer therapy, Parkinsonism, Alzheimer's disease, other degenerative neurological disorders, multiple sclerosis, organ damage during reperfusion after transplant, skin graft rejection, hemorrhagic, traumatic and septic shock, and conditions such as severe burns, ARDS, inflammatory diseases such as osteo- or rheumatoid arthritis, nephrotic syndrome (immunological), systemic lupus erythematosis, allergic reactions, atherosclerosis, inflammation (for example dermatological, inflammatory and psoriasis conditions), emphysema, stress induced ulcers, cluster headaches, complications from brain tumors, radiation damage and damage after MI, infant hypoxia syndrome and such opthalmic disorders such as uveitis and optic neuritis.

In humans, the amino-9,10-secosteroids (I) are useful in preventing damage following cardiopulmonary resuscitation, neurological or cardiovascular surgery and from cardiac infarction.

The amino-9,10-secosteroids (I) are useful for reducing the side effects of the tetracycline anti-neoplastic agents such as adriamycin and daunomycin.

Generally, the amino-9,10-secosteroids (I) are useful in the same way as glucocorticoid pharmaceuticals for the treatment of the above human conditions as well as the animal conditions listed below. While the amino-9,10-secosteroids (I) are useful in both humans and animals in treating many of the same conditions and preventing damage from the same problems as the glucocorticoids, the amino-9,10-secosteroids (I) are useful in treating a number of conditions and preventing damage from conditions where the glucocorticoids are not useful. The amino-9,10-secosteroids (I) have no glucocorticoid activity and therefore, unlike the glucocorticoids, they can be given daily for long periods of time (used chronically) without the side effects associated with the glucocorticoids. This is a distinct advantage.

It is to be understood that each of the amino-9,10-secosteroids (I) is useful to a different degree for treating each of the conditions above. However, as is known to those skilled in the art, some of the amino-9,10-secosteroids (I) are better for treating some conditions and others are better for treating other conditions. In order to determine which compounds are better than others for a particular condition one can utilize known tests that do not require experimentation but only routine analysis.

For example, the fertile egg or chick embryo assay of Folkman, Nature 288, 551 (1980) or Science 221, 719 (1983), discloses an assay to determine antiangiogenic activity which is indicative of inhibition of tumor growth and anti-cancer utility. Because of the ability of the compounds which are active in the Folkman embryo test to inhibit tumor growth, they are useful in the treatment of various diseases and conditions, especially various forms of cancer. Accordingly, they are administered to animals and humans to prolong survival or reduce pain and/or discomfort secondary to tumor growth and the alike. Further, the arachidontic acid $LD_{50}$ test of Kohler, Thrombosis Res., 9, 67 (1976), identifies compounds which are antioxidants, which inhibit lipid peroxidation, and/or which inhibit the prostaglandin cascade and are useful in treating spinal trauma, mild and/or moderate to severe head injury, degenerative neurological disorders, etc. Another method useful for determining which particular compounds inhibit lipid peroxidation and which are therefore useful in treating spinal trauma, mild and/or moderate to severe head injury, degenerative neurological disorders, etc is described by Pryor in Methods of Enzymology 105, 293 (1984). Further, the mouse head injury assay of Hall, J. Neurosurg., 62, 882 (1980) discloses an assay from which one skilled in the art can readily determine which particular amino-9,10-secosteroids (I) are useful in the acute treatment of spinal trauma or mild and/or moderate to severe head injury. Additionally, the cat 48 hr motor nerve degeneration model of Hall et al, Exp. Neurol., 79, 488 (1983) discloses a routine assay from which one skilled in the art can readily determine which particular amino-9,10-secosteroids (I) are useful in treating chronic degenerative neurological disorders such as Parkinsonism, Alzheimer's disease etc. H. Johnson in Int. Arch. Allergy Appl. Immunol., 70, 169 (1983) has described the ascaris sensitized rhesus monkey assay for anti-asthma drugs.

The standard conditions for treatment are to give the amino9,10-secosteroids (I) orally or parenterally, e.g.

IV (that is by injection, infusion or continuous drip) or IM, with a standard dose of about 0.05 to about 100 mg/kg/day, one to four times daily.

For treating spinal trauma, mild and moderate to severe head injury, damage following cardiopulmonary resuscitation, cardiac infarction, organ damage during reperfusion after transplant, hemorrhagic, traumatic and septic shock, severe burns, ARDS, and nephrotic syndrome and preventing skin graft rejection, the standard conditions are used. Typical treatment will involve an initial loading dose, e.g. an IV dose of 0.01 mg to 1 mg/kg followed by maintenance dosing e.g. IV infusion for a day to a week depending on the particular condition of the patient and the particular compound used. This may be supplemented with IM or oral dosing for days, weeks or months to prevent delayed neuronal degeneration in neurological applications (e.g. spinal trauma, head injury).

In treating subarachnoid hemorrhage and subsequent cerebral vasospasm or ischemic (thromboembolic) stroke the standard conditions are used and patients at risk are pre-treated orally.

In treating excess mucous secretion and asthma the amino-9,10-secosteroids (I) are administered orally, IV and by inhalation in the standard dose. In treating excess mucous secretions the dose of the amino-9,10-secosteroids (I) used is from about 0.05 to about 100 mg/kg/day. The frequency of administration is one through 4 times daily. The oral administration of the amino-9,10-secosteroids (I) to treat excess mucous secretions may go on for months or even years. The susceptible individuals can be pre-treated a few hours before an expected problem. The IV does is about 0.05 to about 50 mg/kg/day. The aerosol formulation contains about 0.05 to about 1.0% of the amino-9,10-secosteroids (I) and is administered or used about four times daily as needed.

In treating cancer, muscular dystrophy, Parkinsonism, Alzheimer's disease and other degenerative neurological disorders (amyotrophic lateral sclerosis; multiple sclerosis) the amino-9,10-secosteroids (I) are administered orally using a dose of about 0.05 to about 100 mg/kg/day, administered or used one to four times a day. The treatment may go on for years.

In addition, utility in cancer as well as other disorders or physiological phenomena dependent on angiogenesis or neovascularization such as embryo implantation (antifertility), arthritis, and atherosclerosis is exhibited with the amino-9,10-secosteroids (I) with or without co-administered oral heparin or systemic heparin fragments, see Science 221, 719 (1983).

In treating adriamycin-induced cardiac toxicity and cytotoxicity during anti-cancer therapy the amino-9,10-secosteroids (I) are administered orally or IV using a dose of about 0.05 to about 100 mg/kg/day, preferably about 0.5 to about 10 mg/kg/day. The amino9,10-secosteroids (I) are preferably given concomitantly with IV adriamycin or the individual is pre-treated with the amino-9,10-secosteroids (I).

For prophylaxis prior to and preventing damage after neurological or cardiovascular surgery the amino-9,10-secosteroids (I) are used according to the standard conditions. The patient can be pretreated with a single IV or IM dose just prior to surgery or orally before and after surgery.

In treating osteo- or rheumatoid arthritis and other inflammatory diseases the amino-9,10-secosteroids (I) are given orally or IM in doses of about 0.05 to about 100 mg/kg/day, one to four times daily. Orally the drug will be given over a period of months or years alone or with other steroidal agents. The initial dose with some severe rheumatoid patients may be given IV and followed with an IV drip for up to 24 hr or more. In addition, intra-arterial administration may be employed.

In treating drug allergic reactions the amino-9,10-secosteroids (I) are given in a dose of about 0.05 to 100 mg/kg/day, administered one to four times daily orally and IV. Typical treatment would be an initial IV loading dose followed by oral dosing for a few days or more.

In treating atherosclerosis and emphysema the amino-9,10-secosteroids (I) are given orally in a dose of about 0.05 to about 100 mg/kg/day, one to four times daily for months or years.

In treating dermatological inflammatory conditions including psoriasis the amino-9,10-secosteroids (I) are given orally in a dose of about 0.05 to about 100 mg/kg/day, one to four times daily or applied topically as a cream, ointment or lotion or equivalent dosage form in a concentration of about 0.05 to about 5% as long as needed. In treating these conditions the amino-9,10-secosteroids (I) can be used with steroidal agents.

In treating Alzheimer's disease the amino-9,10-secosteroids (I) are given orally in a dose of about 1 to about 100 mg/kg/day, one to four times daily.

The amino-9,10-secosteroids (I) are useful in the prevention and treatment of stress ulcers and of gastric intolerance caused by drugs such as nonsteroidal anti-inflammatory compounds (NOSAIDS). Stress ulcers are ulcers that develop after exposure to severe conditions such as trauma, burns, sepsis, extensive surgery, acute illnesses, and the like. Patients in intensive care units are particularly prone to develop stress ulcers. Stress ulcers also include lesions that can lead to upper gastrointestinal bleeding; such bleeding is likely to be prevented or stopped by these compounds. NOSAC includes drugs such as ibuprofen, aspirin, indomethacin, naproxen, piroxicam and the like that are usually taken for analgesia, and that are often associated with gastrointestinal intolerance characterized by pain and lesions that may lead to bleeding. The amino-9,10-secosteroids (I) will be administered preferentially by the oral route either as tablets, capsules or liquids, in doses ranging from 5 to 500 mg, two to four times a day. The treatment would be either preventive, i.e., starting before ulcers have formed in patients at risk of developing such lesions, or therapeutic, i.e., after the ulcers have formed. In patients whose clinical condition precludes swallowing the oral dosage forms, the amino-9,10-secosteroids (I) would be given either through a nasogastric tube, or parenterally, i.e., IV or IM. The parenteral doses would range from about 1 to about 100 mg and be administered one to four times a day or by IV.

In dogs, the amino-9,10-secosteroids (I) are useful in treating head and spinal trauma, intervertebral diseases (slipped disk), traumatic shock, flea bite and other allergies.

In horses, the amino-9,10-secosteroids (I) are useful in treating endotoxic or septic shock which follows colic, pretreatment before surgery for colic and treatment of Founder (laminitis).

In cattle, the amino-9,10-secosteroids (I) are useful in treating acute coliform mastitis, bovine mastitis and acute allergic reaction to feed lot vaccination.

In pigs, the amino-9,10-secosteroids (I) are useful in treating porcine stress syndrome and thermal stress syndrome.

The term treatment or treating as used in this patent is used broadly and includes both treatment of an existing condition as well as preventing the same condition from occurring where such is possible as is well known to those skilled in the art. For example, the amino-9,10-secosteroids (I) can be used to treat existing asthma conditions and to prevent future ones from occurring. For example, the amino-9,10-secosteroids (I) treat spinal trauma and prevent rejection of skin grafts.

The amino-9,10-secosteroids (I) can be used with other pharmaceutical agents in treatment of the conditions listed above as is known to those skilled in the art.

The exact dosage and frequency of administration depends on the particular amino-9,10-secosteroids (I) used, the particular condition being treated, the severity of the condition being treated, the age, weight, general physical condition of the particular patient, other medication the individual may be taking as is well known to those skilled in the art and can be more accurately determined by measuring the blood level or concentration of the amino-9,10-secosteroids (I) in the patient's blood and/or the patients response to the particular condition being treated.

DEFINITIONS AND CONVENTIONS

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3-C(=Z_1)H$. Groups $R_i$ and $R_j$ would represent monovalent variable substituents if attached to the formula $CH_3-CH_2-C(R_i)(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the compound nucleus as traditionally designated by those skilled in the art of that chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3-O-CH_2-CH(R_i)-CH_3$ represents a 2-substituted -1-methoxypropane compound. In a similar fashion, the symbol "=" represents a double bond, e.g., $CH_2=C(R_i)-O-CH_3$, and the symbol "≡" represents a triple bond, e.g., $HC≡C-CH(R_i)-CH_2-CH_3$. Carbonyl groups are represents in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by $N^*=C(CH_3)-CH=CCl-CH=C^*H$ with the convention that the atoms marked with an asterisk (*) are bonded to each other resulting in the formation of a ring. Likewise, the cyclic molecular fragment, 4-(ethyl)-1-piperazinyl can be represented by $-N^*-(CH_2)_2-N(C_2H_5)-CH_2-C^*H_2$.

A cyclic (ring) structure for any compound herein defines an orientation with respect to the plane of the ring for substituents attached to each carbon atom of the cyclic compound. In formulas depicting such compounds, a substituent attached to a carbon atom below the plane of the ring is identified as being in the alpha ($\alpha$) configuration and is indicated by a broken, dashed or dotted line attachment to the carbon atom, i.e., by the symbol "— — —" or "...". The corresponding substituent attached above the plane of the ring is identified as being in the beta ($\beta$) configuration. When a variable substituent is bivalent, the valences may be taken together or separately or both in the definition of the variable. For example, a variable $R_i$ attached to a carbon atom as $-C(=R_i)-$ might be bivalent and be defined as oxo or keto (thus forming a carbonyl group (—CO—) or as two separately attached monovalent variable substituents $\alpha$-$R_{ij}$ and $\beta$-$R_{ik}$. When a bivalent variable, $R_i$, is defined to consist of two monovalent variable substituents, the convention used to define the bivalent variable is of the form "$\alpha$-$R_{ij}$:$\beta$-$R_{ik}$" or some variant thereof. In such a case both $\alpha$-$R_{ij}$ and $\beta R_{ik}$ are attached to the carbon atom to yield $-C(\alpha$-$R_{ij})(\beta$-$R_{ik})-$. For example, when the bivalent variable $R_6$, $-(=R_6)-$, (at $C_6$) is defined to consist of two monovalent variable substituents, two monovalent variable substituents are $\alpha$-$R_{6-1}$:$\beta$-$R_{6-2}$, ... $\alpha$-$R_{6-9}$:$\beta$-$R_{6-10}$, etc, yielding $-C(\alpha$-$R_{6-1})(\beta$-$R_{6-2})-$, ... $-C(\alpha$-$R_{6-9})(\beta$-$R_{6-10})-$, etc. Likewise, for the bivalent variable $R_{11}$, $-C(=R_{1-1})-$, (at $C_{11}$) two monovalent variable substituents are $\alpha$-$R_{11-1}$:$\beta$-$R_{11-2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula $-C_1(R_i)H-C_2(R_j)H-$ ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby described an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation "... $R_i$ and $R_j$ are taken together to form —$CH_2$—$CH_2$—O—CO— ... " means a lactone in which the carbonyl is bonded to $C_2$. However, when designated "... $R_j$ and $R_i$ are taken together to form —$CH_2$—$CH_2$—O—CO— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—$(CH_2)_n$—O— CO— where n is zero, one or 2. By the second method the carbon atom content of only each portion of the definition is indicated separately by enclosing the "Ci-Cj" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkyl define alkoxyalkyl groups containing from 2 to 6 carbon atoms, the two definitions differ since the former definition allows either the alkoxy or alkyl portion alone to contain 4 to 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. Definitions

All temperatures are in degrees Centigrade.
TLC refers to thin-layer chromatography.
HPLC refers to high pressure liquid chromatography.
THF refers to tetrahydrofuran.
DMF refers to dimethylformamide.
DMA refers to dimethylacetamide.
p-TSA refers to p-toluenesulfonic acid.
Saline refers to an aqueous saturated sodium chloride solution.
IR refers to infrared spectroscopy.
NMR refers to nuclear (proton) magnetic resonance spectroscopy, chemical shifts are reported in ppm (δ) downfield from tetramethylsilane.
TMS refers to trimethylsilyl.
MS refers to mass spectrometry expressed as m/e or mass/charge unit. [MH]+ refers to the positive ion of a parent plus a hydrogen atom. EI refers to electron impact. CI refers to chemical ionization. FAB refers to fast atom bombardment.
Ether refers to diethyl ether.
Alcohol refers to ethyl alcohol.
When solvent pairs are used, the ratios of solvents used are volume/volume (v/v).

$X_9$ is —H or is taken together with one of the monovalent variable substituents at $X_{11}$ ($X_{11\text{-}1}$ or $X_{11\text{-}2}$) to form a second bond between $C_9$ and $C_{11}$.

$X_{11}$ is =O, —H:-H, α-H:β-OH:β-H or $X_{11\text{-}1}$:$X_{11\text{-}2}$ where one of $X_{11\text{-}1}$ and $X_{11\text{-}2}$ is taken together with $X_9$ to form a second bond between $C_9$ and $C_{11}$.

$X_{17}$ is —C(=Z)—$(CH_2)_n$—OH or =CH—$(CH_2)_p$—OH and hydroxy protected forms thereof, where n and p are as defined in claim 1.

The amino-9,10-secosteroids (I) are also known as octahydro indenones or indenes.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION A-6 4-(2-Pyridinyl)piperazine [34803-66-2], see French Patent No. 7253 M

PREPARATION A-14
4-[4,6-Bis(2-propenylamino)-1,3,5-triazin-2-yl]piperazine

A solution of 2-chloro-4,6-bis(2-propenylamino)-1,3,5-triazine (10.44 g) and 15.95 g of N-formyl piperazine in 150 ml of DMF is heated under reflux for about 18 hours. The reaction mixture is cooled and stored at 5° and crystals are deposited. The soluble fraction is concentrated and the residue is extracted with ethyl acetate. The extracts are washed with aqueous potassium carbonate, 50% saline, saline and dried over magnesium sulfate and concentrated to give a gum. Chromatography on silica gel (400 g) and elution (200 ml fractions) with 20% acetone-methylene chloride gives the formamide. The formamide (9.2 g) in 200 ml of methanol is heated to reflux, then cooled under nitrogen and mixed with 4 ml of 45% potassium hydroxide solution. The mixture is heated under reflux for about 20 hours, then cooled and concentrated. The residue is partitioned between ethyl acetate and water. The organic extracts are washed with water and saline, dried over magnesium sulfate and concentrated to give a gum. Crystallization from 50 ml of carbon tetrachloride gives the title compound, mp 93–94.5°.

PREPARATION A-22
4-[2,6-Bis(1-pyrrolidinyl)-4-pyrimidinyl]piperazine

A solution of pyrrolidine (80 g) in THF (500 ml) is chilled in an ice water bath and stirred mechanically under nitrogen. With a syringe pump of 2,4,6-trichloropyrimidine (50 g) is added over 35 minutes. The reaction is stirred in the ice bath for 1 hour and is then warmed to 20–25° over 4 h. Pyridine (100 ml) is added to the reaction and the mixture stirred at 20–25° overnight. The reaction is concentrated. The residue is partitioned between methylene chloride and aqueous sodium bicarbonate. The organic phase is concentrated and the residue chromatographed on silica gel (10% ethyl acetate/hexane) to yield 51 g of crystalline 2,4-bis[pyrrolidino]-6-chloropyrimidine. Immediately after the initial addition of reagents, two spots are seen with 25% ethyl acetate on a silica gel plate. These are the 2- and the 4- adducts. The bis product forms over time. It moves between these first two spots. The 51 g of product is reacted with piperazine (40 g) in 100 ml of dry pyridine at 100° for 50 h. The reaction is concentrated. The residue is partitioned between methylene chloride and sodium bicarbonate solution. The organic phase is dried and concentrated. The residue is chromatographed on silica gel eluting with methylene chloride to 10% methanol/1% ammonia/methylene chloride to give the title compound, NMR (CDCl$_3$) 1.90, 2.9, 3.35 and 4.80 δ.

PREPARATION A-23
4-[2,6-Bis(morpholino)-4-pyrimidinyl]piperazine

A solution of 160 g of morpholine in 1000 ml of methylene chloride is treated dropwise with 100 g of 2,4,6-trichloropyrimidine. The reaction is immersed in an ice water bath. After 1 h, 300 ml of pyridine is added. The reaction is stirred for two days and concentrated. The residue is partitioned between methylene chloride and aqueous sodium bicarbonate. The residue is chromatographed on silica gel (10% ethyl acetate/hexane to 25% to methylene chloride) to give 2,4-[bis(morpholino)]-6-chloropyrimidine. A solution of 40 g of 2,4-[bis-morpholino]-6-chloropyrimidine and 34 g of piperazine in 60 g of pyridine is heated at 100° for 24 h. The mixture is partitioned between methylene chloride and aqueous potassium carbonate. The organic phase is filtered through sodium sulfate and concentrated. The residue is chromatographed (methylene chloride to 4% methanol/1% ammonium hydroxide/methylene chloride) to give the title compound, NMR (CDCl$_3$) 2.90, 3.50, 3.75, 3.80 and 5.10 δ.

PREPARATION A-24
4-[2,6-Bis(allylamino)-4-pyrimidinyl]piperazine

Following the general procedure for PREPARATION A-22, and making non-critical variation but substituting allylamine for pyrrolidine the title compound is obtained.

PREPARATION A-25 4-(2-Pyrimidinyl)piperazine
[20980-22-7]See U.S. Pat. No. 4,409,223

PREPARATION A-26
4-[4,6-Bis(diethylamino)-2-pyrimidinyl]piperazine

Diethylamine (80 g) is reacted with trichloropyrimidine (50 g) in THF. The reaction after chromatography yields a mixture of the mono- and di-adduct. This material is dissolved in pyridine (58 g) and reacted with diethylamine (35 g) at 50° for 3 h. The reaction is concentrated to a residue. The residue is partitioned between methylene chloride and aqueous sodium bicarbonate. The organic phase is separated and concentrated. The residue is chromatographed on silica gel, eluting with ethyl acetate/hexane (10/90). The appropriate fractions are pooled and concentrated to give 2,4-bis[diethylamino]-6-chloropyrimidine. This material is dissolved in pyridine (100 g) and reacted with piperazine (40 g) at 100° for 50 h. Following the above workup procedure the title compound is obtained, NMR (CDCl$_3$) 1.15, 2.90, 3.45 and 4.9 δ.

PREPARATION A-45
4-[4,6-Bis(1-pyrrolidinyl)-1,3,5-triazin-2-yl]-1-piperazine Pyrrolidine (28.5 g) is cooled with an ice bath. 1,3,5-Trichlorotriazine (18.4 g) is added with vigorous stirring. After 1–1.5 h the mixture is permitted to warm to 20–25°. The solid is filtered and rinsed several times with water and dried under reduced pressure to give the monochloro-bis(1-pyrrolidinyl)triazine.

This material (23.18 g) in piperazine (31.55 g) at DMF (295 ml) is refluxed under nitrogen. When the reaction is complete (TLC) the solvent is removed under reduced pressure. The mixture is transferred to a separatory funnel containing ethyl acetate (100 ml) and potassium carbonate (100 ml). The layers are separated, the organic layer is washed with saline (100 ml) and back-washed with ethyl acetate (2×100 ml). The organic layers are combined, dried over magnesium sulfate at room temperature, filtered and concentrated under reduced pressure. This material is chromatographed on a silica gel column (500 g) eluting with acetone/methylene chloride (5/95). The appropriate fractions (500 ml) are pooled and concentrated to give a solid.

The solid (10.13 g) is refluxed in methanol (200 ml) and cooled under nitrogen. Potassium hydroxide (45% aqueous, 4 ml) is added, the mixture degassed with nitrogen and heated to reflux. After 8 h the mixture is cooled to room temperature and concentrated under reduced pressure. The solid is transferred to a separatory funnel containing ethyl acetate (200 ml) and water (100 ml). The phases are separated, the organic layer is washed with water (2×100 ml) and 50% brine (100 ml) followed by brine (2×100 ml). The aqueous washes are back-washed with 200 ml of ethyl acetate, the organic phases are combined, dried over magnesium sulfate, filtered, concentrated under reduced pressure to give the title compound, m.p. 162.5–166°.

PREPARATION A-46
4-[3,6-Bis(diethylamino)-2-pyridinyl]piperazine

Diethylamine (3.29 ml) is added dropwise over 1 h to a mixture of 2,6-dichloro-3-nitropyridine (6.13 g), acetonitrile (100 ml) and potassium carbonate (5.2 g) precooled to 0°. The mixture is allowed slowly to warm to 20–25° and stirred for 16 h. The mixture is filtered, the filtrate combined with piperazine (12.2 g) and potassium carbonate (6 g). The resulting mixture is heated at reflux for 24 h and then permitted to cool to 20–25°. Aqueous workup (methylene chloride, water washed over organic layers, potassium carbonate) and purification by flash chromatography (silica gel) eluting with chloroform/methanol (20:1 25:1) gives 6-N,N-diethylamino-3-nitro-2-(1-piperazinyl)pyridine.

This material (21.8 g), ethanol (275 ml), hydrochloric acid (1.2N, 27 ml) and 10% palladium on charcoal (5.25 g) is exposed to hydrogen at 50 pounds per square inch in a Parr flask. After 16 h the residue is filtered through celite, concentrated and partitioned between chloroform and sodium hydroxide (5%). The organic layers are separated, dried using potassium carbonate, concentrated. The concentrate is passed through a plug of silica gel, eluting with chloroform/methanol/ammonium hydroxide (4/1/0.25) to give 3-amino-6-N,N-diethylamino-2-(1-piperazinyl)pyridine.

A solution of di t-butyl dicarbonate (11.8 g) and methylene chloride (25 ml) is added dropwise over 30 min to a mixture of 3-amino-6-N,N-diethylamino-2-(1- piperazinyl)pyridine (13.5 g), triethylamine (8.33 ml) and methylene chloride (400 ml) precooled to 0°. The resulting mixture is allowed to slowly warm to 20–25°. After 16 h using basic workup (methylene chloride, sodium bicarbonate, potassium carbonate) the t-butyl carbonate as a solid is obtained.

The protected piperazinyl pyridine (4 g) acetaldehyde (12.8 ml), acetonitrile (80 ml) is mixed. Sodium cyanoborohydride (1.73 g) is added to the pyridine mixture. The resultant solution is stirred for 48 h at 20–25°. After 24 h additional sodium cyanoborohydride (500 ml) and acetaldehyde (5 ml) is added. Basic workup (chloroform/potassium carbonate, potassium carbonate) and purification by flash chromatography using silica gel and eluting with hexane ethyl acetate (5/1) gives an oil. The oil (2.36 g), ethyl acetate (50 ml), and hydrochloric acid (3.0 N, 37.5 ml) are stirred for 16 h at 20–25°. Basic workup (chloroform, 10% sodium hydroxide, potassium carbonate) gives the title compound, MS (electron impact) 305.

PREPARATION A-47
4-[3-(Ethylamino)-2-pyridinyl]-piperazine 2-(1-Piperazinyl)-3-nitropyridine (24.50 g), ethanol (445 ml) and hydrochloric acid (1.2N, 44 ml) are combined and hydrogenated overnight at 40 psi initial pressure in a Parr Bomb, refilling when necessary. The mixture is filtered through celite, washed with ethanol, chloroform, ethanol and water. The organic solvents are removed with head and reduced pressure. The remaining material is partitioned between methylene chloride (3×250 ml) and sodium bicarbonate. The organic layers are combined, dried over potassium carbonate, filtered and concentrated under reduced pressure to give an oil which slowly solidified upon standing to give 3-amino-2-(1-piperazinyl)pyridine.

3-Amino-2-(1-piperazinyl)pyridine (19.58 g), methylene chloride 600 ml), triethylamine (17.2 ml) are combined and cooled to 6°. Dit-butyl-dicarbonate (24.34 g) in methylene chloride (50 ml) is added to the pyridine mixture over 30 min and permitted to stand at 0° for 1 hr, then allowed to warm to 20–25°. After 30 min, TLC indicates no starting material remains. The reaction mixture is partitioned between sodium bicarbonate (500 ml) and methylene chloride (3×250 ml). The organic phases are combined, dried over potassium carbonate, filtered and concentrated under reduced pressure and heat to give a solid which is recrystallized from ethyl acetate to give 3-amino-2-[(4-t-butyoxycarbonyl)-1-piperazinyl]pyridine.

3-Amino-2-[(4-t-butoxycarbonyl)-1-piperazinyl]pyridine (2.361 g), methanol (23.6 ml) and acetaldehyde (2.1 ml) are combined at 20–25° to form a solution. Sodium cyanoborohydride (586 mg) is added and the mixture stirred overnight. The organic solvent is removed with reduced pressure and heat, the remaining mixture is partitioned between sodium bicarbonate (50 ml) and chloroform (3×50 ml). The chloroform extracts are combined and dried over potassium carbonate and filtered. The filtrate is concentrated with heat and reduced pressure. The concentrate is column chromatographed on silica gel 60 (40 63µ) eluting with hexane/ethyl acetate (2/1) containing triethylamine (1%). The appropriate fractions are pooled and concentrated to give 3-ethylamino-2-[(4-t-butylcarbonyl)-1-piperazinyl]pyridine.

3-Ethylamino-2-[(4-t-butylcarbonyl)-1-piperazinyl]-pyridine (2.47 g), ethyl acetate (67 ml) and hydrochloric acid (3N, 49 ml) are combined and stirred for 2 hr at 20–25°. TLC indicates no starting material. Potassium hydroxide (14 g) and water (80 ml) is added. The organic layer is removed and extracted with chloroform (3×60 ml). The organic layers are combined, dried over potassium carbonate, filtered and the filtrate concentrated to give the title compound, NMR (CDCl₃) 1.25, 1.50, 3.1, 3.5, 6.90 and 7.75 δ.

PREPARATION A-48
4-[3-(Diethylamino)-2-pyridinyl]piperazine

Following the general procedure of PREPARATION A-47 and making non-critical variations but reacting the protected ethylamine compound with additional acetaldehyde and again reducing the title compound is obtained, NMR (CDCl₃) 0.95, 3.25, 6.80, 7.20 and 7.90 δ.

PREPARATION A-49
4-[4,6-Bis(2-pyridinyl)-1,3,5-triazin-2-yl]piperazine

A mixture of 4-formyl-piperazinecarboximidamide hydroiodide (prepared according to U.S. Pat. No. 4,351,832) in ethanol (4 ml) and ethanolic sodium ethoxide (1.4N, 6.8 ml) is stirred for 15 min, then 2-cyanopyridine (2.08 g) is added. The mixture is concentrated at atmospheric pressure and heated at about 200° for 5 hr, then cooled and chromatographed on silica gel eluting with methanol/methylene chloride (30/70). The appropriate fractions are pooled and concentrated to give the 1-formyl 4-[4,6-bis(2-pyridinyl)-1,3,5-triazin-2-yl]piperazine. Hydrolysis of the formamide in the usual way (PREPARATION A-14) gives the title compound.

PREPARATION A-51
4-[2,6-Bis(2-pyridinyl)-4-pyrimidinyl]-piperazine

4-Chloro-2,6-bis(2-pyridinyl)pyrimidine [prepared by the method of J.A.C.S. 32, 1591 (1967), 4.2 g] piperazine (13.44 g) and ethanol (70 ml) is heated at reflux for 2 hr. The mixture is allowed to cool and the solvent is removed under reduced pressure. The residue is dissolved in chloroform (250 ml), washed with water (twice), dried over sodium sulfate and concentrated under reduced pressure to give an oil. The oil is crystallized from ether to give the title compound, mp 159–161°; MS (m/e) 318 (M+).

PREPARATION A-55
3,6-Bis(2-pyridinyl)-4-pyridazine

PREPARATION A-56
6-Methoxy-2-morpholino-4-(1-piperazinyl)pyrimidine

A solution of 2,4,6-trichloropyrimidine (55 g), methanol (50 ml) and collidine (50 g) is heated in dry tetrahydrofuran (400 ml) for 48 hr. Ether is added and the precipitate is collected. The precipitate is column chromatographed on silica gel to give 6-methoxy-2,4-dichloropyrimidine. This product is mixed with morpholine in THF and stirred at 20–25° to give 6-methoxy-2-morpholino-4-chloropyrimidine. The 6-methoxy-2-morpholino-4-chloropyrimidine is heated with piperazine in pyridine at 60° for 24 hr to give the title compound.

PREPARATION A-57 4-(3-Chlorophenyl)piperazine

[65369-76-8], see Aldrich catalog, 1986-7, 12,518-0

PREPARATION A-58
1-[2-(3-Diethylamino)pyridinyl]piperazine

Sodium cyanoborohydride (3.06 g) is added to a solution of 1-[2-(3-ethylamino)pyridinyl]-4-(t-butyoxycarbonyl)piperazine (5.38 g), acetaldehyde (5.0 ml) and methanol (54 ml). The mixture is stirred for 10 days at 20-25°. Acetaldehyde (5.0 ml) is added at 2, 3, 4 and 7 days. Sodium cyanoborohydride (3.06 g) is added at 3 and 7 days. After 10 days no further change in the reaction occurred as measured by TLC. Basic workup (chloroform/sodium bicarbonate/magnesium sulfate) gives an oil. The crude residue is resubmitted to the above reaction conditions. After 5 days the reaction is worked up as described above. Purification by flash chromatography (hexane/ethyl acetate; 5/1) provides the carbamate of the title compound, NMR (CDCl$_3$) 0.98, 1.49, 3.21, 3.35-3.65, 6.82, 7.16 and 7.92 δ; IR (neat) 2974, 1699, 1577, 1438, 1234 and 1172 cm$^{-1}$; MS (EI) m/e (relative percent) 334 (79), 205 (64), 178 (45), 162 (56), 57 (100).

The carbamate (1.17 g), ethyl acetate (29.0 ml) and hydrochloric acid (3N, 21.2 ml) are stirred at 20-25° for 1.5 hr. Potassium hydroxide (8 g) and water (30 ml) are added. Aqueous workup (chloroform/potassium carbonate) gives the title compound, IR (nujol) 2957, 2925, 1574, 1450, 1259 and 776 cm$^{-1}$; NMR (CDCl$_3$) 0.96, 3.16, 3.15-3.3, 3.7-3.85, 6.84, 7.17 and 7.91 δ; MS (EI, relative percent) 234 (60), 178 (66), 162 (100) and 148 (67).

PREPARATION A-59
1-(5-Diethylamino-2-pyridinyl)piperazine

2-Chloro-5-nitropyridine (25 g) is dissolved in acetonitrile (150 ml) and the mixture is added dropwise over 30 min to a stirred suspension of piperazine (61.3 g) and potassium carbonate (26.2 g) in acetonitrile (550 ml). The reaction mixture is stirred at 20-25° for 16 hr. The solvent is removed on a rotary evaporator and the residue is diluted with methylene chloride/water. The organic layer is separated and washed with water (twice) and saline, dried over potassium carbonate and concentrated to give 1-(4-nitro-2-pyridinyl)piperazine, IR 3338, 3102, 3068, 1603, 1570, 1482, 1347, 1340, 1320, 1306 and 1253 cm$^{-1}$.

The nitro compound (30.7 g) is dissolved in ethanol (500 ml), and palladium/carbon (10%, 10 g) and hydrochloric acid (1.2N, 55 ml) are added and the mixture hydrogenated on a Parr apparatus (50 psi) for 4 hr. The mixture is then filtered thru celite and the filtrate evaporated to dryness to give an oil. The residue is partitioned between saturated sodium bicarbonate and chloroform, the layers are separated, the aqueous layer is reextracted with chloroform (2×250 ml) and the organic phases are combined, dried over potassium carbonate and concentrated under reduced pressure. The pH of the aqueous phase is raised to 11 by the addition of solid potassium hydroxide, the mixture reextracted with chloroform, dried and concentrated to give the crude 4-amino compound. The aqueous layer is concentrated to half the volume, excess sodium chloride is added and the mixture is reextracted with chloroform. The extract is dried and concentrated to obtain additional 4-amino compound.

The amine (21 g), triethylamine (17.9 g) and methylene chloride (600 ml) are cooled to 0°. Di-t-butyl dicarbonate (25.8 g) in methylene chloride (200 ml) is added over 30 min at 0°. The reaction mixture is stirred at 0° for 1 hr and allowed to warm to 20-25°. The reaction mixture is washed with saturated sodium bicarbonate (3×200 ml), dried over potassium carbonate and the solvent removed under reduced pressure to give a solid. The solid is dissolved in ether, petroleum ether is added until the mixture is cloudy, the mixture is filtered thru celite and the filtrate is concentrated to give the protected piperazine compound.

The piperazine protected compound (2.6 g) and acetaldehyde (1.7 g) in methanol (25 ml) is cooled to 0°. Sodium cyanoborohydride (0.62 g) is added in one portion. The cooling bath is removed and the mixture is permitted to warm to 20°. The mixture is stirred at 20-25° for 2 hr. The methanol is removed under reduced pressure and the residue is partitioned between methylene chloride and a saturated sodium bicarbonate solution. The phases are separated and the organic phase is washed with saturated sodium bicarbonate solution, saline, dried over magnesium sulfate and concentrated under reduced pressure to give an oil. The oil is purified by HPLC on silica gel, MS (M$^+$) 234.

The oil (2.1 g), aqueous hydrochloric acid (3N, 42 ml) and ethyl acetate (57 ml) are stirred for 1 hr at 20-25°. The mixture is cooled in ice, basified (pH=11) with potassium hydroxide (20%), the phases separated and the aqueous phase extracted again with ethyl acetate. The combined extracts are washed with saline, dried over magnesium sulfate, and concentrated under reduced pressure to give the title compound. NMR was in agreement.

PREPARATION A-60
1-[4-(5Ethylamino-6-diethylamino)pyrimidinyl]piperazine

A solution of di-t-butyldicarbonate (4.78 g) and methylene chloride (20 ml) is added to a mixture of 1-[4-(5-amino-6-diethylamino)pyrimidinyl]piperazine (4.97 g), methylene chloride (70 ml), triethylamine (3.33 ml) and dimethylaminopyridine (10 mg). The mixture is stirred overnight. Basic workup (sodium bicarbonate/methylene chloride/magnesium sulfate) and purification by flash chromatography (hexane/ethyl acetate; 2/1) gives the carbamate of 1-[4-(5-amino-6-diethylamino)pyrimidinyl]piperazine, MS (EI, relative percent) 350 (100), 251 (38), 207 (38) and 194 (89).

Sodium cyanoborohydride (0.300 g) is added to a solution of the carbamate (0.652 g), methanol (13 ml) and acetaldehyde (2.1 ml). The mixture is stirred for 1 week at 20-25°. At two day intervals similar amounts of sodium cyanoborohydride and acetaldehyde are added. Concentration and basic workup (chloroform/sodium bicarbonate/magnesium sulfate) and purification by flash chromatography (hexane/ethyl acetate; 2/1) give the t-butyl carbamate of the title compound, MS (EI, relative percent) 378 (100), 322 (21), 293 (43), 277 (18) and 249 (44).

The carbamate of the title compound (465 mg), ethyl acetate (9.5 ml) and hydrochloric acid (3N, 7 ml) are stirred at 20-25° for 2 hr. Basic workup (chloroform/solid potassium hydroxide/magnesium sulfate) provide the title compound, NMR (CDCl$_3$) 1.06, 1.07, 2.98, 2.95-3.1, 3.25 and 3.35-3.45 δ.

PREPARATION A-61

4-(5-amino-6-diethylamino)pyrimidinylpiperazine

A solution of diethylamine (4.0 ml) and acetonitrile (25 ml) is added dropwise over 40 min to a mixture of 4,6-dichloro-5-nitropyrimidine (7.5 g), acetonitrile (150 ml) and potassium carbonate (6.41 g) at 0°. The mixture is stirred for an additional 50 min at 0° and is then allowed to warm to 20–25°. After 16 hr, the mixture is filtered, and the residue washed with acetonitrile (2×25 ml).

The crude filtrate, piperazine (25.8 g) and potassium carbonate (6.41 g) are combined and heated at reflux for 6 hr. After cooling to 20–25°, basic workup (sodium bicarbonate/chloroform/magnesium sulfate) and purification by flash chromatography (chloroform/methanol/ammonium hydroxide; 200/10/1) an oil is obtained which solidifies upon standing to give 5-nitro-6-diethylamino-4-piperazinylpyrimidine, MS (CI, relative percent) 281 (100), 265 (13), 249 (18) and 234 (71).

5-Nitro-6-diethylamino-4-piperazinylpyrimidine (0.980 g), ethanol (25 ml) and palladium/carbon (10%, 0.25 g) are exposed to hydrogen (50 psi) for 24 hr. The mixture is filtered and the residual solids are washed with chloroform/ethanol. The combined filtrates are concentrated under reduced pressure. Basic workup (aqueous potassium hydroxide, chloroform, magnesium sulfate) provided a solid, mp 58–59°; NMR (CDCl$_3$) 1.11, 2.95–3.05, 3.15–3.4 and 3.29 $\delta$.

EXAMPLE 1

11$\beta$,17$\alpha$,21-Trihydroxypregna-1,4-diene-3,20-dione 17,21-acetonide A solution of 11$\beta$,17$\alpha$,21-trihydroxypregna-1,4-diene-3,20-dione (13.0 g), dimethoxypropane (166 ml), p-TSA (278 mg) and DMF (83 ml) is heated at reflux for 6 hours. The reaction is quenched with sodium bicarbonate (1.19 g), cooled to 20–25°, filtered and concentrated to a solid. The solid is flash chromatographed on silica gel, eluting with ethyl acetate/hexane (1/1). The appropriate fractions are pooled and concentrated to give the title compound, mp 232–235°; IR (nujol) 3385, 1715, 1657 cm$^{-1}$; NMR (CDCl$_3$) 1.39, 1.42, 4.16, 4.49, 6.01, 6.27 and 7.28 $\delta$; MS (EI) 342 and 121.

EXAMPLE 2

17$\alpha$,21-Dihydroxypregna-1,4-diene-3,11,20-trione 17,21-acetonide

11$\beta$,17$\alpha$,21-Trihydroxypregna-1,4-diene-3,20-dione 17,21-acetonide (EXAMPLE 1, 25.6 g) is added to a mixture of pyridinium chlorochromate (20.7 g), anhydrous sodium acetate (1.56 g) and methylene chloride (130 ml) at 20–25°. After 2 hours, ether (300 ml) is added and the mixture filtered through a pad of florasil. The precipitate is washed with ether (180 ml) and chloroform (300 ml). The filtrates are combined and concentrated to a solid which is flash chromatographed on silica gel, eluting with ethyl acetate/hexane (1/1). The appropriate fractions are pooled and concentrated to obtain the title compound, mp 200.5–201.5°; IR (nujol) 1718, 1709 and 1662 cm$^{-1}$; NMR (CDCl$_3$) 1.44, 4.16, 6.09, 6.22 and 7.68 $\delta$; MS (FAB) 399, (MH+).

EXAMPLE 3

Octahydro-4′-[2-(5-hydroxy-2-methylphenyl)ethyl]2,2,7′a-trimethylspiro[1,3-dioxane-4,1′[1H]-indene]5,6′(2′H)-dione Lithium (20 mg) is added to liquid ammonia (1200 ml) at −78°. In a second flask, 17$\alpha$,21-dihydroxypregna-1,4-diene-3,11,20-trione 17,21-acetonide, (EXAMPLE 2, 14.0 g) is added to freshly distilled THF (280 ml) under nitrogen. The anhydrous ammonia is allowed to condense into the second flask. To this mixture is added lithium (716 mg) in chunks periodically over 2 hours at reflux. The lithium uptake is monitored by the loss of blue color to yellow. Ammonium chloride (5.90 g) is added to the mixture and the ammonia allowed to evaporate at 20–25°. The mixture is concentrated to a solid and partitioned between chloroform and water (1/1, 400 ml). Hydrochloric acid (10%) is added to the mixture until the pH is about 8. The layers are separated and the aqueous layer is extracted with chloroform (2×200 ml). The organic layers are combined and washed with water (2×100 ml), dried over sodium sulfate and concentrated to a solid. The solid is flash chromatographed on silica gel, eluting with chloroform/methanol (50/1). The appropriate fractions are pooled and concentrated to give the title compound, mp 226–227.5°; IR (nujol) 3280, 1718, 1683, 1620 and 1586 cm$^{-1}$; NMR (CDCl$_3$) 1.44, 1.49, 2.19, 4.16, 4.82, 6.4–6.6 and 6.9–7.0 $\delta$; MS (FAB) 401 (MH+) and 121.

EXAMPLE 4

Octahydro-4′-[2-[2-methyl-5-(phenylmethoxy)phenyl]ethyl]-2,2,7′a-trimethylspiro[1,3-dioxane-4,1′[1H]indene]-5,6′(2′H)-dione A mixture of octahydro-4′-[2-(5-hydroxy-2-methylphenyl(ethyl]-2,2,7′a-trimethylspiro[1,3-dioxane-4,1′[aH]-indene]-5,6′(2′H)-dione (EXAMPLE 3, 4.85 g) methylene chloride (55 ml), benzyl bromide (2.28 g), tetrabutylammonium hydrogen sulfate (535 ml) and sodium hydroxide (50%, 26 ml) are stirred at 20–25° for 3 hours. The mixture is distributed between chloroform and water. The layers are separated, the aqueous layer is extracted with chloroform (2×50 ml). The organic layers are combined and partitioned with water (100 ml). Hydrochloric acid (10%) is added until the aqueous layer is neutralized. The organic layer is dried over sodium sulfate and concentrated to an oil which crystallizes upon standing to give the title compound, mp 121–124; IR (nujol) 1718, 1701, 1617 and 1580 cm$^{-1}$; NMR (CDCl$_3$) 1.44, 1.49, 2.21, 4.16, 5.20, 6.7–6.8, 7.0–7.1 and 7.3–7.5 $\delta$; MS (FAB) 490, 433, and 91.

EXAMPLE 5

3a-Methyl-3$\alpha$-hydroxy-7-[2-(5-phenylmethoxy-2-methylphenyl)-ethyl]-3-(2-hydroxyacetyl)octahydro-5H-indene-5-one A mixture of octahydro-4′-[2-[2-methyl-5-phenylmethoxy)phenyl]ethyl]-2,2,7′a-trimethylspiro[1,3-dioxane-4,1′[1H]-indene]-5,6′(2′H)dione (EXAMPLE 4, 5.90 g), THF (50 ml) and hydrochloric acid (1N, 50 ml) is stirred at 20–25° for 22 hours. Additional portions of hydrochloric acid (1N, 10 ml) are added at approximately 24 hour intervals over 4 days. Excess amounts of sodium bicarbonate are added and the mixture is concentrated to a solid. The solid is partitioned between chloroform and water. The phases are separated and the aqueous phase is extracted with chloroform (2×100 ml). The organic layers are combined, washed with water, dried over sodium sulfate and concentrated to an oil. The oil is flash chromatographed on silica gel, eluting with ethyl acetate/hexane (3/2, 800 ml) and ethyl acetate (1 liter). The appropriate fractions are pooled and concentrated to give the title compound, mp 95–97; IR (nujol) 3416, 1723, 1688 and 1610 cm$^{-1}$; NMR (CDCl$_3$)2.21, 4.42, 5.02, 6.6–6.8, 7.0–7.1 δ; MS (FAB) 450, 91.

EXAMPLE 6

3a-Methyl-3α-hydroxy-7-[2-(5-phenylmethoxy-2-methylphenyl)-ethyl]-3-(2-chloroacetyl)-octahydro-5H-indene-5-one and
3a-methyl-3α-hydroxy-7-[2-(5-phenylmethoxy-2-methylphenyl)-ethyl]-3-(2-tosyloxyacetyl)-octahydro-5H-indene-5-one A mixture of 3a-methyl-3α-hydroxy-7-[2-(5-phenylmethoxy-2-methylphenyl)-ethyl]-3-(2-hydroxyacetyl)octahydro-5H-indene-5-one (EXAMPLE 5, 2.20 g) pyridine (17 ml) and p-toluenesulfonyl chloride (1.02 g) is stirred at 0° for 1.5 hours. The mixture is allowed to warm to 20–25° and stirred for 3 hours. The pyridine is removed under reduced pressure and the residue is partitioned between chloroform and hydrochloric acid (1N). The layers are separated and the aqueous layer is extracted with ethyl acetate/chloroform (1/1, 4 ×150 ml). The organic layers are combined, washed with water (twice), dried over sodium sulfate and concentrated to an oil. The oil is flash chromatographed on silica gel, eluting with chloroform/methanol (50/1). The appropriate fractions are pooled and concentrated to give the title compound as an oil. IR (nujol) 3363, 1734, 1688, 1614 and 1579 cm$^{-1}$; NMR (CDCl$_3$) 2.21, 4.42, 5.02, 6.6–6.8, 7.0–7.1 and 7.3–7.5 δ; MS (FAB) 468, 470 and 91.

EXAMPLE

3a-Methyl-3α-hydroxy-7-[2-[2-methyl-5-(phenylmethoxy)phenyl]ethyl]-3-[2-[4-(2,6-bis(1-pyrrolidinyl)-4-pyrimidinyl)-1-piperazinyl]acetyl]octahydro-5H-inden-5-one (I)

A mixture of 3a-methyl-3α-hydroxy-7-[2-(5-phenylmethoxy-2-methylphenyl)-ethyl]-3-(2-chloroacetyl)-octahydro-5H-indene-5-one and 3a-methyl-3α-hydroxy-7-[2-(5-phenylmethoxy-2-methylphenyl)-ethyl]-3-(2-tosyloxyacetyl) -octahydro-5H-indene-5-one (EXAMPLE 6, 1.16 g), 4-[(2,6-bis(1-pyrrolidinyl)-4-pyrimidinyl]piperazine (published PCT patent application Ser. No. 86/01797, PREPARATION A-22, 0.930 g), potassium carbonate (748 mg), and acetonitrile (31 ml) are heated at reflux for 28 hours. The acetonitrile is removed under reduced pressure and the residue is taken up in chloroform and saline. The layers are separated, the aqueous phase is extracted with chloroform (2×100 ml). The organic phases are combined, washed with water (100 ml), dried over sodium sulfate and concentrated to give a solid. The solid is flash chromatographed on silica gel, eluting with ethyl acetate/hexane (4/1). The appropriate fractions are pooled and concentrated to give the title compound, IR (nujol) 1708 cm$^{-1}$; NMR (CDCl$_3$) 1.7–2.0, 2.21, 2.4–2.7, 3.2–3.7, 4.83, 5.02, 6.6–6.8, 7.0–7.1 and 7.3–7.5 δ; MS (FAB) 735 (MH$^+$) and 246.

EXAMPLE 7A

3a-Methyl-3α-hydroxy-7-[2-[2-methyl-5-(phenylmethoxy)phenyl]ethyl]-3-[2-[4-(2,6-bis(1-pyrrolidinyl)-4-pyrimidinyl)-1-piperazinyl]acetyl]-octahydro-5H-inden-5-one hydrochloride (I)

The hydrochloride salt of the amino-9,10-secosteroid (I) of EXAMPLE 7 is prepared by methods well known to those skilled in the art, mp 180–187° (dec).

EXAMPLE 8

3a-Methyl-3α-hydroxy-7-[2-(5-hydroxy-2-methylphenyl)ethyl]-3-[2-[4-(2,6-bis(1-pyrrolidinyl)-4-pyrimidinyl)-1-piperazinyl]acetyl]octahydro-5H-inden-5one (I)

A mixture of 3a-methyl-3α-hydroxy-7-[2-[2-methyl-5-(phenylmethoxy)phenyl]ethyl]-3-[2-[4-(2,6-bis(1-pyrrolidinyl)-4-pyrimidinyl)-1-piperazinyl]acetyl]-octahydro-5H-inden-1-one (EXAMPLE 7, 1.12 g), cyclohexene (20 ml), 10% palladium on carbon (0.28 g), ethyl acetate (10 ml) and ethanol (5 ml) is heated at reflux under nitrogen. After 3 hours additional 10% palladium on carbon (0.12 g) is added and the mixture heated at reflux overnight. The mixture is cooled to 20–25° filtered through celite and concentrated to a solid. The solid is flash chromatographed on silica gel, eluting with chloroform/methanol (17/1). The appropriate fractions are pooled and concentrated to give the title compound, IR 3324 and 1708 cm$^{-1}$; NMR (CDCl$_3$) 1.7–2.0, 2.21, 2.4–2.7, 3.2–3.7, 4.83, 6.5–6.6, 6.9–7.0 δ; MS (FAB) 645 (MH+) and 246.

EXAMPLE 8A

3a-Methyl-3α-hydroxy-7-[2-(5-hydroxy-2-methylphenyl)ethyl]-3-[2
-[4-(2,6-bis(1-pyrrolidinyl)-4-pyrimidinyl)-1-piperazinyl]acetyl]octahydro-5H-inden-5-one fumarate (I)

Following the general procedure of EXAMPLE 7A and making noncritical variations but starting with the compound of EXAMPLE 8 and using fumaric acid, the title compound is obtained, mp 120–127° (dec).

EXAMPLE 9

3a-Methyl-3α-hydroxy-7-[[2-methyl-5-(phenylmethoxy)phenyl]ethyl]-3-[2-[4-(2-pyridinyl)-1-piperazinyl]acetyl]octahydro-5H-inden-5-one (I)

Following the general procedure of EXAMPLE 7 and making noncritical variations but starting with 1-(2-pyridinyl)piperazine (34803-66-2, French patent No. 7253 M, and published PCT patent application Ser. No. 86/01797, PREPARATION A-6) the title compound is obtained, mp 77–84°; IR (nujol) 3434, 1703, 1673 and 1592 cm$^{-1}$; NMR (CDCl$_3$) 2.20, 2.4–2.7, 3.4–3.7, 5.02, 6.6–6.8, 7.0–7.1, 7.3–7.6 and 8.1–8.2 δ; MS(FAB) 596 (MH$^1$), 594, 176 and 91.

EXAMPLE 10

3a-Methyl-3α-hydroxy-7-[2-(5-hydroxy-2-methylphenyl)ethyl]-3-[2
-[4-(2-pyridinyl)-1-piperazinyl]acetyl]octahydro-5H-inden-5-one (I)

Following the general procedure of EXAMPLE 8 and making noncritical variations but starting with the compound of EXAMPLE 9, the title compound is obtained, IR (nujol) 3448, 1720, 1674 and 1591 cm$^{-1}$;

NMR (CD₃OD/CDCl₃) 2.18, 3.5–3.7, 6.5–6.7, 6.9–7.0, 7.4–7.6 and 8.1–8.2 δ; MS (FAB) 506 (MH¹), 176 and 121.

EXAMPLE 10A

3a-Methyl-3α-hydroxy-7-[2-(5-hydroxy-2-methylphenyl)ethyl]-3-[2-[4-(2-pyridinyl)-1-piperazinyl]acetyl]octahydro-5H-inden-5-one hydrochloride (I)

Following the general procedure of EXAMPLE 7A and making noncritical variations but starting with the compound of EXAMPLE 10 and using hydrochloric acid, the title compound is obtained, mp 170–177° (dec).

EXAMPLE 11

3a-Methyl-3α-hydroxy-7-[[2-methyl-5-(phenylmethoxy)phenyl]ethyl]-3-[2-[4-[3-(ethylamino)-2-pyridinyl]-1-piperazinyl]acetyl]-octahydro-5H-inden-5-one (I)

Following the general procedure of EXAMPLE 7 and making noncritical variations but starting with 4-[3-(ethylamino)-2-pyridinyl]piperazine (published PCT patent application Ser. No. 86/01797, PREPARATION A-47) the title compound is obtained, IR (nujol) 3363, 1708, 1608, and 1580 cm⁻¹; NMR (CDCl₃) 2.21, 2.9–3.4, 3.9–4.2, 5.02, 6.6–7.1, 7.3–7.5 and 7.6–7.7; MS (FAB) 639 (MH¹), 219 and 91.

EXAMPLE 12

3a-Methyl-3α-hydroxy-7-[2-(5-hydroxy-2-methylphenyl)ethyl]-3-[2-[4-[3-(ethylamino)-2-pyridinyl]-1-piperazinyl]acetyl]-octahydro-5H-inden-5-one (I)

Following the general procedure of EXAMPLE 8 and making noncritical variations but starting with 3a-methyl-3α-hydroxy-7-[[2-methyl-5-(phenylmethoxy)phenyl]ethyl]-3-[2-[4-[3-(ethylamino)-2-pyridinyl]-1-piperazinyl]acetyl]-octahydro-5H-inden-5-one (EXAMPLE 11), the title compound is obtained, IR (nujol) 3355, 1707, 1610 and 1580 cm⁻¹; NMR (CDCl₃) 2.2, 3.0–3.4, 4.0–4.2, 6.6–7.1 and 7.6–7.7 δ; MS (FAB) 549 (MH¹) and 219.

EXAMPLE 12A

3a-Methyl-3α-hydroxy-7-[2-(5-hydroxy-2-methylphenyl)ethyl]-3-[2-[4-[3-(ethylamino)-2-pyridinyl]-1-piperazinyl]acetyl]-octahydro-5H-inden-5-one dihydrochloride dihydrate (I)

Following the general procedure of EXAMPLE 7A and making noncritical variations but starting with 3a-methyl-3α-hydroxy-7-[2-(5-hydroxy-2-methylphenyl)ethyl]-3-[2-[4-[3-(ethylamino)-2-pyridinyl]-1-piperazinyl]acetyl]-octahydro-5H-inden-5-one (EXAMPLE 12) and using ethereal hydrochloric acid and recrystallizing from methanol/ether, the title compound is obtained, mp 167–173° (dec).

EXAMPLE 13

3a-Methyl-7-[2-(5-hydroxy-2-methylphenyl)-ethyl]-3-(2-hydroxyethylidene)-octahydro-5H-inden-5-one Following the general procedure of EXAMPLE 3 and making noncritical variations but starting with 21-hydroxypregna-1,4,17(20)trien-3-one [Steroids, 3, 189 (1964), 2.30 g] the title compound is obtained, MS (EI) 310 (M-H₂O); NMR (CDCl₃) 2.20, 4.1–4.4, 5.1, 5.4–5.5, 6.5–6.7 and 6.99 δ; IR (nujol) 3373 and 1700 cm⁻¹.

EXAMPLE 14

3a-Methyl-7-[2-(5-hydroxy-2-methylphenyl)-ethyl]-3-(2-hydroxyethyl)-3α-octahydro-5H-inden-5-one 3a-Methyl-7-[2-(5-hydroxy-2-methylphenyl)-ethyl]-3-(2-hydroxyethylidene)-octahydro-5H-inden-5-one (EXAMPLE 13, 2.30 g) is placed in a Parr bomb with palladium on carbon (10%, 0.46 g). Ethanol (46 ml) is added. The Parr bomb is then flushed with nitrogen (3 ×) and hydrogen (3×). The pressure is then brought to 50 lb/in² and stirred for 1.5 hr. The mixture is filtered using celite and the filtrate removed under reduced pressure. The solid is chromatographed by eluting with ethyl acetate/hexane (70/30). The appropriate fractions are pooled and concentrated to give the title compound, mp 150–152°.

EXAMPLE 15

3a-Methyl-7-[2-(5-hydroxy-2-methylphenyl)-ethyl]-3-(2-chloroethyl)-3α-octahydro-5H-inden-5-one Triphenylphosphine (1.77 g) and carbon tetrachloride (7.0 ml) are mixed in a flask with a condenser. In a second flask 3a-methyl7-[2-(5-hydroxy-2-methylphenyl)ethyl]-3-(2-hydroxyethyl)-3α-octahydro-5H-inden-5-one (EXAMPLE 14, 1.49 g), acetonitrile (9 ml) and chloroform (7.5 ml) are mixed. The contents of the two flasks are combined and stirred at 20–25° for 30 min then heated at 55° for 5 hr. The mixture is then taken up in chloroform/saline (60 ml/60 ml) and extracted with chloroform (2×). The chloroform extracts are combined and washed with saline (60 ml), dried over sodium sulfate, concentrated, and chromatographed eluting with ethyl acetate/hexane (33/67). The appropriate fractions are pooled, concentrated and recrystallized from ethyl acetate/hexane to give the title compound, mp 166–167°; MS (EI) 350, 348, 227, 213 and 122.

EXAMPLE 16

3a-Methyl-7-[2-(5-hydroxy-2-methylphenyl)-ethyl]-3-[2-[4-(2,6-bis(1-pyrrolidinyl)-4-pyrimidinyl)-1-piperazinyl]ethyl]-3α-octahydro-5H-inden-5-one (I)

3a-Methyl-7-[2-(5-hydroxy-2-methylphenyl)-ethyl]-3-(2-chloroethyl)-3α-octahydro-5H-inden-5-one (EXAMPLE 15, 52 mg), 4-[2,6-bis(1-pyrrolidinyl)-4-pyrimidinyl]piperazine (PREPARATION A-22, 68 mg), sodium iodide (67 mg) and potassium carbonate (46 mg) are mixed and flushed with nitrogen. Acetonitrile (1.2 ml) is added by a syringe and the mixture is stirred at 20–25° for 15 min followed by heating at 80° for 27 hr. Additional acetonitrile (0.3 ml) is added and the mixture stirred 4 hr. DMF (0.3 ml) is added. Four hours later additional DMF (0.3 ml) is added and the mixture is heated at 90° overnight. The mixture is taken up in chloroform/saline. Hydrochloric acid (10%) is added dropwise to pH 8. The phases are separated, the aqueous phase is extracted with chloroform, the chloroform extracts are combined, washed with water (2 ×), dried over sodium sulfate and concentrated. The concentrate is flash chromatographed on silica gel eluting with methanol/chloroform (5/95) containing a trace of ammonium hydroxide. The appropriate fractions are pooled and concentrated to give the title compound, NMR (CDCl₃) 1.8–2.0, 2.19, 2.4–2.5, 3.3–3.6, 4.85, 6.5–6.6 and 6.97 δ; MS (EI) 614, 246 and 233.

EXAMPLE 17

3a-methyl-7-[2-(5-hydroxy-2-methylphenyl)-ethyl]-3-[2-[4-[3-(ethylamino)-2-pyridinyl]-1-piperazinyl]ethyl]-3α-octahydro-5H-inden-5-one (I)

4-[3-(Ethylamino)-2-pyridinyl]piperazine (PREPARATION A-47, 361 mg), 3a-methyl-7-[2-(5-hydroxy-2-methylphenyl)ethyl]-3-(2-chloroethyl)-3α-octahydro-5H-inden-5-one (EXAMPLE 15, 349 mg), sodium iodide (450 mg) and sodium carbonate (304) are mixed and the flask is flushed with nitrogen. DMF (6 ml) is added by a syringe. The mixture is stirred at 20–25° for 15 min, then heated at 90° overnight. The mixture is taken up in chloroform/saline and the phases are separated. The aqueous phase is extracted with chloroform (2×40 ml), the organic phases are combined, washed with water (3×100 ml) and dried over sodium sulfate. The mixture still contains some DMF. The mixture is taken up in chloroform/water (50 ml/50 ml), the phases are separated, the chloroform phase is washed with water (3×50 ml), dried over sodium sulfate and concentrated. The concentrate is flashed chromatographed following the procedure of EXAMPLE 16 to give the title compound, NMR (CDCL$_3$) 1.30, 2.19, 3.0–3.2, 4.1–4.2, 6.5–6.6, 6.80, 6.85–6.95, 6.97 and 7.70 δ; MS (EI) 518 and 371.

EXAMPLE 17A

3a-Methyl-7-[2-(5-hydroxy-2-methylphenyl)-ethyl]-3-[2-[4-[3-(ethylamino)-2-pyridinyl]-1-piperazinyl]ethyl]-3α-octahydro-5H-inden-5-one oxalate (I)

Following the general procedure of EXAMPLE 7A and making non-critical variations but starting with the compound of EXAMPLE 7 and using oxalic acid, the title compound is obtained, mp 134–139°.

EXAMPLE 18

3a-Methyl-3α-hydroxy-7-[2-(5-hydroxy-2-methyl-phenyl)ethyl]-3-[2-[4-[2,6-bis(2-pyridinyl)-4-pyrimidinyl]-1-piperazinyl]acetyl]octahydro-5H-inden-5-one (I)

Following the general procedure of EXAMPLE 17 and making noncritical variations but starting with 3a-methyl-3α-hydroxy-7-[2-(5-hydroxy-2-methylphenyl)ethyl]-3-(2-chloroacetyl)-octahydro-5H-indene-5-one and 3a-methyl-3α-hydroxy-7-[2-(5-hydroxy-2-methylphenyl)-ethyl]-3-(2-tosyloxyacetyl)-octahydro-5H-indene-5-one (EXAMPLE 6) and 4-[2,6-bis(2-pyridinyl)-4-pyrimidinyl]piperazine (PREPARATION A-51), the title compound is obtained.

EXAMPLE 19

3a-Methyl-7-[2-(5-hydroxy-2-methylphenyl)-ethyl]-3-(2-chloroethylidene)-octahydro-5H-inden-5-one Following the general procedure of EXAMPLE 15 and making noncritical variations but starting with 3a-methyl-7-[2-(5-hydroxy-2-methylphenyl)-ethyl]-3-(2-hydroxyethylidene)-octahydro-5H-inden-5-one (EXAMPLE 13) the title compound is obtained.

EXAMPLE 20

3a-methyl-7-[2-(5-hydroxy-2-methylphenyl)ethyl]-3-[2-[4-[3-(ethylamino)-2-pyridinyl]-1-piperazinyl]ethylidene]-3α-octahydro-5H-inden-5-one (I)

Following the general procedure of EXAMPLE 17 and making noncritical variations but starting with 3a-methyl-7-[2-(5-hydroxy-2-methylphenyl)ethyl]-3-(2-chloroethylidene)octahydro-5H-inden-5-one (EXAMPLE 19) and 4-[3-(ethylamino)-2-pyridinyl]piperazine (PREPARATION A-47), the title compound is obtained.

EXAMPLE 21

21-hydroxypregna-1,4-diene-3,11,20-trione

17α,21-Dihydroxypregna-1,4-diene-3,11,20-trione [JACS 77, 4438 (1955),3.226 g] is placed in a flask and flushed with nitrogen. Freshly distilled acetonitrile (225 ml) are added and the mixture cooled to 0°. Trimethylsilyl iodide (TMS-I, 5.12 ml) is added dropwise. After 30 minutes sodium sulfite (5%, 150 ml) is added followed by chloroform (400 ml). The phases are separated and the aqueous phase is extracted with chloroform (2×100 ml). The organic phases are combined, washed with sodium bicarbonate (5%, 150 ml) followed by a saline wash. The organic phase is then dried over sodium sulfate and concentrated. The concentrate is flashed chromatographed on silica gel, eluting with ethyl acetate. The appropriate fractions are pooled and concentrated to a solid. The solid is dissolved in ethyl acetate/hexane and an impurity is crystallized and filtered off. The filtrate, containing the title compound, is concentrated and rechromatographed on silica gel eluting with ethyl acetate/hexane (70/30). The appropriate fractions are pooled and concentrated to give the title compound.

EXAMPLE 22

3a-Methyl-7-[2-(5-hydroxy-2-methylphenyl)ethyl]-3-(2-hydroxyacetyl)-3α-octahydro-5H-inden-5-one Following the general procedure of EXAMPLE 3 and making noncritical variations but starting with 21-hydroxypregna-1,4-diene3,11,20-dione (EXAMPLE 21) the title compound is obtained.

EXAMPLE 23

3a-Methyl-7-[2-(5-hydroxy-2-methylphenyl)ethyl]-3-(2-chloroacetyl)-3α-octahydro-5H-inden-5-one Following the general procedure of EXAMPLE 15 and making noncritical variations but starting with 3a-methyl-7-[2-(5-hydroxy-2-methylphenyl)ethyl]-3-(2-hydroxyacetyl)-3α-octahydro-5H-inden-5-one (EXAMPLES 22 or 38) the title compound is obtained.

EXAMPLE 24

3a-Methyl-7-[2-(5-hydroxy-2-methylphenyl)ethyl]-3-[2-[4-[3-(ethylamino)-2-pyridinyl]-1-piperazinyl]acetyl]-3α-octahydro-5H-inden-5-one (I)

Following the general procedure of EXAMPLE 17 and making noncritical variations but starting with 3a-methyl-7-[2-(5-hydroxy-2-methylphenyl)-ethyl]-3-(2-chloroacetyl) -3α-octahydro-5H-inden-5-one (EXAMPLE 23) and 4-[3-(ethylamino)-2-pyridinyl]piperazine (PREPARATION A-47), the title compound is obtained.

EXAMPLE 25

3a-Methyl-7-[2-(5-hydroxy-2-methylphenyl)ethyl]-3-(2-bromoethylidene) -octahydro-5H-inden-5-one Following the general procedure of EXAMPLE 15 and making noncritical variations but starting with 3a-methyl-7-[2-(5-hydroxy-2-methylphenyl)-ethyl]-3-(2-hydroxyethylidene)-octahydro-5H-inden-5-one (EXAMPLE 13) and using carbon tetrabromide in place of carbon tetrachloride, the title compound is obtained, MS (EI) 392 and 390; NMR (CDCl$_3$) 0.94, 1.61–2.1, 2.20, 2.3–2.8, 2.94, 4.0–4.2, 4.9, 5.4–5.5, 6.5–6.7 and 6.99 δ.

EXAMPLE 26

3a-methyl-7-[2-(5-hydroxy-2-methylphenyl)-ethyl]-3-[2-[4-[3-(ethylamino)-2-pyridinyl]-1-piperazinyl]ethylidene]-3α-octahydro-5H-inden-5-one (I)

Following the general procedure of EXAMPLE 17 and making noncritical variations but starting with 3a-methyl-7-[2-(5-hydroxy-2-methylphenyl)-ethyl]-3-(2-bromoethylidene)-octahydro-5H-inden-5-one (EXAMPLE 25) and 4-[3-(ethylamino)-2-pyridinyl]piperazine (PREPARATION A-47), the title compound is obtained, MS (EI) 516 and 501; NMR (CDCl$_3$) 0.78, 1.31, 1.4–1.5, 1.7–2.1, 2.57, 2.3–2.7, 2.97, 3.0–3.2, 4.1–4.2, 5.25–5.35, 6.58, 6.63, 6.91, 6.98 and 7.70 δ.

EXAMPLE 26A 3a-methyl-7-[2-(5-hydroxy-2-methylphenyl)-ethyl-3-[2-[4-[3-(ethylamino)-2-pyridinyl]-1-piperazinyl]ethylidene]-3α-octahydro-5H-inden-5-one - hydrochloride (I)

Following the general procedure of EXAMPLE 7A and making noncritical variations but starting with the compound of EXAMPLE 26 and using hydrochloric acid, the title compound is obtained, mp 182–188°.

EXAMPLE 27

3a-methyl-7-[2-(5-hydroxy-2-methylphenyl)-ethyl]-3-[2-[4-(2, 6-bis(1-pyrrolidinyl)-4-pyrimidinyl]-1-piperazinyl]ethyl]-3α-octahydro-5H-inden-5-one (I)

Following the general procedure of EXAMPLE 16 and making noncritical variations but starting with 3a-methyl-7-[2-(5-hydroxy-2-methylphenyl)ethyl]-3-(2-bromoethylidene)-octahydro-5H-inden-5-one (EXAMPLE 25) and 4-[(2,6-bis(1-pyrrolidinyl)-4-pyrimidinyl]-piperazine (PREPARATION A-22), the title compound is obtained, MS (EI) 612; NMR (CDCl$_3$) 0.89, 1.35–1.50, 1.5–1.7, 1.8–2.0, 2.3–2.6, 2.6–2.7, 2.91, 3.3–3.5, 3.5–3.6, 4.85, 5.25–5.35, 6.56, 6.60 and 6.98 δ; IR (nujol) 1706 cm$^{-1}$.

EXAMPLE 28

21-Hydroxypregna-1,4-diene-3,11,20-trione and 17-epi-21-hydroxypregna-1,4-diene-3,11,20-trione Trimethylsilyl iodide (5.12 ml, 7.20 g, 36.0 mmol) is added dropwise to a solution of 17α,21-dihydroxypregna-1,4-diene-3,11,20-trione (3.23 g) in freshly distilled acetonitrile. After 30 min, sodium sulfite solution (5%, 150 ml) is added to the reaction mixture. The mixture is partitioned with chloroform (400 ml). The phases are separated, and the aqueous phases is extracted twice with chloroform. The organic layers are combined, washed with sodium bicarbonate (5%), saline, dried over sodium sulfate and concentrated. The concentrate is flash chromatographed eluting with ethyl acetate/hexane (2.3/1). The appropriate fractions are pooled to give 21-hydroxypregna-1,4-diene-3,11,20-trione as an oil and 17-epi-21-hydroxypregna-1,4-diene-3,11,20-trione as a solid, mp 203–206°.

EXAMPLE 29

3a-Methyl-7-[2-(5-hydroxy-2-methylphenyl)ethyl]-3αacetyl-3β-octahydro-5H-inden-5-one A solution of 17-epi-21-hydroxypregna-1,4-diene-3,11,20-trione (EXAMPLE 28, 0.14 g) in freshly distilled THF (5 ml) is added dropwise to a solution of lithium (24 mg) in distilled ammonia (50 ml) at −78°. After 30 min ammonium chloride (300 mg) is added and the ammonia is allowed to evaporate overnight. The mixture is partitioned between chloroform and saline, the layers separated and the aqueous layer is extracted twice with chloroform. The organic phases are combined, washed with saline, dried over sodium sulfate and concentrated to a solid. The solid is flash chromatographed on silica gel eluting with hexane/ethyl acetate (3/2, 300 ml) and hexane/ethyl acetate (2/3, 200 ml). The appropriate fractions are pooled and concentrated to give a solid, mp 159–160°; MS (EI) 328, 313 and 285.

EXAMPLE 30

3a-Methyl-7-[2-(5-hydroxy-2-methylphenyl)ethyl]-3α-(2-bromoacetyl)-3β-octahydro-5H-inden-5-one 3a-Methyl-7-[2-(5-hydroxy-2-methylphenyl)ethyl]-3α-acetyl-3β-octahydro-5H-inden-5-one (EXAMPLE 29) is treated with bromine (1 equivalent) in acetic acid to give the title compound.

EXAMPLE 31

3a-Methyl-7-[2-(5-hydroxy-2-methylphenyl)ethyl]-3α-[2-[4-(2,6-bis(1-pyrrolidinyl)-4-pyrimidinyl)-1-piperazinyl]acetyl]-3β-octahydro-5H-inden-5-one (I)

Following the general procedure of EXAMPLES 16 and 17 and making non-critical variations but starting with 3a-methyl-7-[2-(5-hydroxy-2-methylphenyl)ethyl]-3α-(2-bromoacetyl)-3β-octahydro-5H-inden-5-one (EXAMPLE 30) and 4-[(2,6-bis(1-pyrrolidinyl)-4-pyrimidinyl]piperazine (PREPARATION A-22), the title compound is obtained.

EXAMPLE 32

3a-Methyl-7-[2-(5-hydroxy-2-methylphenyl)ethyl]-3α-[2[4-[3-(ethylamino)-2-pyridinyl]-1-piperazinyl]acetyl]3β-octahydro-5H-inden-5-one (I)

Following the general procedure of EXAMPLES 16 and 17 and making non-critical variations but starting with 3a-methyl-7-[2-(5-hydroxy-2-methylphenyl)ethyl]-3α-(2-bromoacetyl-3β-octahydro-5H-inden-5-one (EXAMPLE 30) and 4-[3-(ethylamino)-2-pyridinyl]piperazine (PREPARATION A-47), the title compound is obtained.

EXAMPLE 33 Pregna-1,4-diene-3,11,20-trione

11α-Hydroxypregna-1,4-diene-3,20-dione (120 mmol) in acetone (950 ml) is treated with Jones reagent (38.7 ml) at 0°. Following work-up the title compound is obtained.

EXAMPLE 34
3a-Methyl-7-[2-(5-hydroxy-2-methylphenyl)ethyl]-3-(2-acetyl)-3α-octahydro-5H-inden-5-one Following the general procedure of EXAMPLE 3 and making noncritical variations but starting with pregna-1,4-diene-3,11,20-trione (EXAMPLE 33) the title compound is obtained.

EXAMPLE 35
3a-Methyl-7-[2-(5-hydroxy-2-methylphenyl)ethyl]-3-(2-bromoacetyl)-3α-octahydro-5H-inden-5-one Following the general procedure of EXAMPLE 30 and making noncritical variations but with 3a-methyl-7-[2-(5-hydroxy-2-methylphenyl)ethyl]-3-(2-acetyl)-3α-octahydro-5H-inden-5-one (EXAMPLE 34) the title compound is obtained.

EXAMPLE 36
3a-Methyl-7-[2-(5-hydroxy-2-methylphenyl)ethyl]-3β-[2[4-[3-(ethylamino)-2-pyridinyl]-1-piperazinyl]acetyl]-3α-octahydro-5H-inden-5-one (I)

Following the general procedure of EXAMPLES 16 and 17 and making non-critical variations but starting with 3a-methyl-7-[2-(5-hydroxy2-methylphenyl)ethyl]-3β-(2-bromoacetyl)-3α-octahydro-5H-inden-5-one (EXAMPLE 30) and 4-[3-(ethylamino)-2-pyridinyl]piperazine (PREPARATION A-47), the title compound is obtained.

EXAMPLE 37
3a-Methyl-3β-acetoxyacetyl-7-[2-(5-hydroxy-2-methylphenyl)ethyl]-3α-octahydro-5H-inden-5-one Following the general procedure of Cocker, et al., J. Chem. Soc., 6 (1965) 3a-methyl-7-[2-(5-hydroxy-2-methylphenyl)ethyl]-3-(2-acetyl)-3α-octahydro-5H-inden-5-one (EXAMPLE 34) is treated with boron trifluoride/ether and lead tetraacetate in methanol/benzene (5/95) at 20–25°. After 3 hr the reaction mixture is quenched with water and the product extracted with ether and crystallized to give the title compound.

EXAMPLE 38
3a-Methyl-3β-hydroxyacetyl-7-[2-(5-hydroxy-2-methylphenyl)ethyl]-3α-octahydro-5H-inden-5-one 3a-Methyl-3β-acetoxyacetyl-7-[2-(5-hydroxy-2-methylphenyl)ethyl]-3α-octahydro-5H-inden-5-one (EXAMPLE 37) is treated with anhydrous sodium carbonate in methanol and stirred at 20–25° for 5.5 hr. The excess base is neutralized with ammonium chloride and the resulting solution is concentrated under reduced pressure to a solid which is partitioned between chloroform and water (1/1). The aqueous layer is further extracted with chloroform and combined with the organic layer. The organic phase is dried over sodium sulfate, concentrated under reduced pressure to give the title compound.

EXAMPLE 39
3a-Methyl-3β-[2-[4-[3,6-bis(diethylamino)-2-pyridinyl]-1-piperazinyl]acetyl]-7-[2-(5-hydroxy-2-methylphenyl)ethyl]-3α-octahydro-5H-inden-5one (I)

Following the general procedure of EXAMPLES 16 and 17 and making non-critical variations but starting with 3a-methyl-7-[2-(5-hydroxy-2-methylphenyl)ethyl]-3-(2-chloroacetyl)-3α-octahydro-5H-inden-5-one (EXAMPLE 23) and 4-[3,6-bis(diethylamino)-2-pyridinyl]-piperazine (PREPARATION A-46), the title compound is obtained.

EXAMPLE 40
7a-Methyl-1β-acetyl-4α-[2-(5-hydroxy-2-methylphenyl)ethyl]-2, 3, 3aα, 4, 7, 7a-hexahydro-Δ$^5$-1H-indene Following the procedure of Ananthamarayan, et al, J. C. S. Chem. Commun., 709 (1982), 11α-hydroxypregna-1,4-diene-3,20-dione 11-xanthate is added to samarium iodide (4 equivalents) prepared from samarium metal and 4 equivalents of freshly prepared 1,2-diodoethane in THF. The mixture is stirred for 5 min at 20–25° then quenched in cold hydrochloric acid (10% aqueous) and extracted with ethyl acetate. The ethyl acetate layer is washed with sodium thiosulfate, dried over sodium sulfate and concentrated under reduced pressure. The concentrate is chromatographed over silica gel by eluting with chloroform/hexane/ethyl acetate (95/5/1). The appropriate fractions are pooled and concentrated to give the title compound, mp 153–154°.

EXAMPLE 41
7a-Methyl-1β-(2-bromoacetyl)-4α-[2-(5-hydroxy-2-methylphenyl)-ethyl]-2, 3, 3aα, 4, 7, 7a-hexahydro-Δ$^5$-1H-indene Following the procedure of Elks, et al, J. Chem. Soc., 4001 (1958) the methyl ketone is selectively brominated in the presence of the double bond using bromine in methylene chloride containing ether. The reaction mixture is cautiously added to cold saline and extracted with ether. The combined organic layers are dried over sodium sulfate and concentrated under reduced pressure. Flash chromatography provides the title compound.

EXAMPLE 42
7a-Methyl-1β-[2-[4-[3-(ethylamino)-2-pyridinyl]-1-piperazinyl]acetyl]-4α-[2-(5-hydroxy-2-methylphenyl)ethyl]-2, 3, 3aα, 4, 7, 7a-hexahydro-Δ$^5$-1 H-indene (I)

Following the general procedure of EXAMPLES 16 and 17 and making non-critical variations but starting with 7a-methyl-1β-(2-bromoacetyl)-4α-[2-(5-hydroxy-2-methylphenyl)-ethyl]-2, 3, 3aα, 4, 7, 7a-hexahydro-Δ$^5$-1H-indene (EXAMPLE 41) and 4-[3-(ethylamino)-2-pyridinyl]piperazine (PREPARATION A-47), the title compound is obtained.

EXAMPLE 43
7a-Methyl-4α-[2-(5-hydroxy-2-methylphenyl)-ethyl]-1β-[2-[4-(2,6-bis(1-pyrrolidinyl)-4-pyrimidinyl)-1-piperazinyl]acetyl]-2, 3, 3aα, 4, 7, 7a-hexahydro-Δ$^5$-1H-indene (I)

Following the general procedure of EXAMPLES 16 and 17 and making non-critical variations but starting with 7a-methyl-1β-(2-bromoacetyl)-4α-[2-(5-hydroxy-2-methylphenyl)-ethyl]-2, 3, 3aα, 4, 7, 7a-hexahydro-Δ$^5$-1H-indene (EXAMPLE 41) and 4-[(2,6-bis(1-pyrrolidinyl)-4-pyrimidinyl]piperazine (PREPARATION A-22), the title compound is obtained.

CHART A

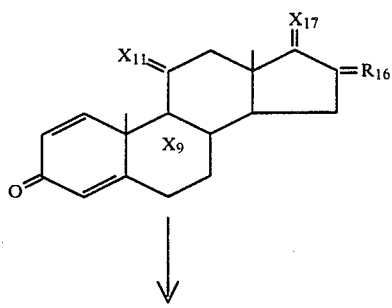

-continued
CHART A

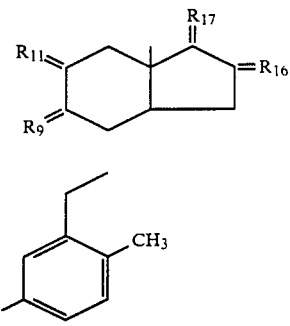

(I)

CHART B

| Name | Chemical Structure | Formula No. |
|---|---|---|
| pyridin-2-, | [pyridine with $(R_{21-2})_{0-2}$ substituent and $(O)_{0-1}$ on N] | (F-1) |
| 3-, | [pyridine with $(R_{21-2})_{0-2}$ substituent and $(O)_{0-1}$ on N] | (F-2) |
| or 4-yl optionally substituted optionally as the N-oxide | [pyridine with $(R_{21-2})_{0-2}$ substituent and $N{-}(O)_{0-1}$] | (F-3) |
| $-*CH_2-(CH_2)_c-G-(CH_2)_d-CH_2-N*-$ | [ring: $-*N$, $*CH_2-(CH_2)_c$, $G$, $CH_2-(CH_2)_d$] | (F-4) |
| 3-pyrrolin-1-yl | [$-N$ pyrroline ring] | (F-5) |
| pyrrol-1-yl optionally substituted | [$-N$ pyrrole with $(C_1-C_3\ alkyl)_{0-1}$] | (F-6) |
| piperidin-1-yl optionally substituted | [$-N$ piperidine with $(C_1-C_3\ alkyl)_{0-1}$ and $(C_2-C_3\ alkyl)_{0-1}$] | (F-7) |
| 1,2,3,6-tetrahydropyridin-1-yl | [$-N$ tetrahydropyridine ring] | (F-8) |

CHART B-continued

| Name | Chemical Structure | Formula No. |
|---|---|---|
| 1-hexamethyleneimino containing a 3- or 4- double bond or 3- and 5- double bonds | 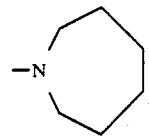 | (F-9) |
| 1,4-dihydro-1-pyridinyl substituted in the 4-position | 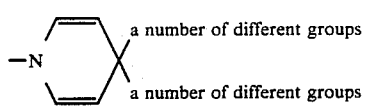 a number of different groups / a number of different groups | (F-10) |
| 1,3,5-triazin-2-yl or the $N_1$-oxide thereof optionally substituted at the 4- and/or 6-position | 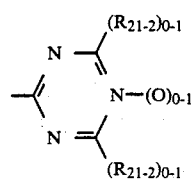 $(R_{21-2})_{0-1}$ / $N-(O)_{0-1}$ / $(R_{21-2})_{0-1}$ | (F-11) |
| pyrimidin-4-yl or the $N_1$-oxide thereof optionally substituted at the 2- and/or 6- and 5- and/or 6-position | 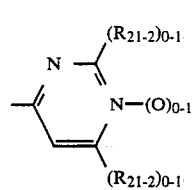 $(R_{21-2})_{0-1}$ / $N-(O)_{0-1}$ / $(R_{21-2})_{0-1}$ | (F-12) |
| pyrimidin-2-yl optionally substituted | 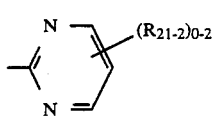 $(R_{21-2})_{0-2}$ | (F-13) |
| pyrazin-2-yl optionally substituted | 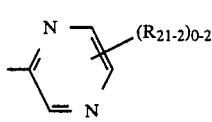 $(R_{21-2})_{0-2}$ | (F-14) |
| imidazol-2-yl optionally substituted in | 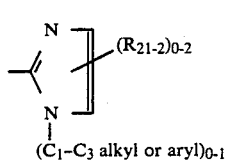 $(R_{21-2})_{0-2}$ / $(C_1-C_3$ alkyl or aryl$)_{0-1}$ | (F-15) |
| 1,3,4-triazol-2-yl optionally substituted | 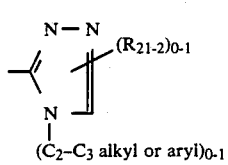 $(R_{21-2})_{0-1}$ / $(C_2-C_3$ alkyl or aryl$)_{0-1}$ | (F-16) |
| imidazol-4- or 5-yl optionally substituted | 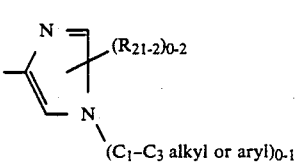 $(R_{21-2})_{0-2}$ / $(C_1-C_3$ alkyl or aryl$)_{0-1}$ | (F-17) |
| benzo[b]thien-2-yl | 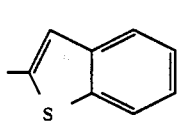 | (F-18) |

CHART B-continued

| Name | Chemical Structure | Formula No. |
|---|---|---|
| indol-2-yl | (structure) | (F-19) |
| benzo[b]thiazol-2-yl | (structure) | (F-20) |
| benzimidazol-2-yl | (structure) | (F-21) |
| 4-[2- [4-[2,6-di-(1-pyrrolidinyl)-4-pyrimidinyl]-1-piperazinyl]ethyl]-piperazinyl | $-N\frown N-CH_2CH_2-N\frown N$ — (pyrimidinyl with 2,6-di-pyrrolidinyl) | (F-22) |
| 1,2,4-triazin-3-yl optionally substituted at the 5- and/or 6- position | (triazine ring with $(R_{21-2})_{0-1}$ substituents) | (F-23) |
| (1-piperazinyl)-($C_2$–$C_4$) optionally substituted in the 4-position | $-(C_2-C_4 \text{ alkyl})-N\frown N-(\text{aryl or heteroaryl})$ | (F-24) |
| (1-piperazinyl)acetyl substituted in the 4-position | $-CO-CH_2-N\frown N-\text{heteroaryl}$ | (F-25) |
| (1-piperazinyl)carbonylmethyl substituted in the 4-position | $-CH_2-CO-N\frown N-\text{heteroaryl}$ | (F-26) |
| 2-(carboxyl)-1-pyrrolidinyl | (pyrrolidine with COOH) | (F-27) |
| 2-(carboxy)-1-piperidinyl | (piperidine with COOH) | (F-28) |

CHART B-continued

| Name | Chemical Structure | Formula No. |
|---|---|---|
| 2-(carboxy)-1-hexamethyleneimino | 7-membered N-ring with COOH at 2-position | (F-29) |
| 2-(carboxy)-1-heptamethyleneimino | 8-membered N-ring with COOH at 2-position | (F-30) |
| 1-piperazinyl substituted in the 4-position | $-N\!\!\!\bigcirc\!\!\!N-(CH_2)_j-CO-R_{21\text{-}12}$ | (F-31) |
| 1-piperazinyl substituted in the 4-position | $-N\!\!\!\bigcirc\!\!\!N-(CH_2)_j\text{-heteroaryl}$ | (F-32) |
| 1-piperazinyl substituted in the 4-position | $-N\!\!\!\bigcirc\!\!\!N-(CH_2)_j\text{-aryl}$ | (F-33) |
| 4-hydroxy-1-piperidinyl substituted in the 4-position | piperidine with OH and aryl at 4-position | (F-34) |
| 1-piperazinyl substituted in the 4-position | $-N\!\!\!\bigcirc\!\!\!N-(CH_2)_j-CO-NR_{21\text{-}13}\text{-heteroaryl}$ | (F-35) |
| 1-(4-methyl)piperazinyl | $-N\!\!\!\bigcirc\!\!\!N-CH_3$ | (F-36) |
| 1-(4-acetyl)piperazinyl | $-N\!\!\!\bigcirc\!\!\!N-CO-CH_3$ | (F-37) |
| 1-(4-hydroxy)piperidinyl | piperidine with OH at 4-position | (F-38) |
| 1-piperidinyl optionally substituted with 2-hydroxyethyl | piperidine with $CH_2CH_2OH$ at 4-position | (F-39) |
| 4-morpholinyl | morpholine ring | (F-40) |

We claim:
1. An amino-9,10-secosteroid of formula I

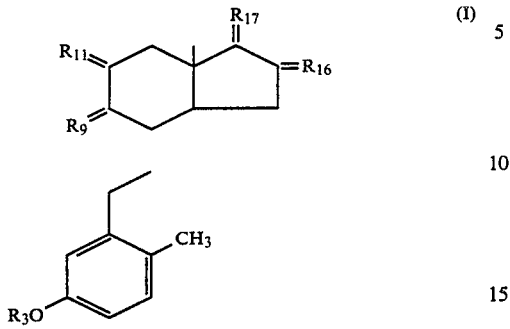

where:
$R_3$ is —H or —CO—$R_{3-1}$ where $R_{3-1}$ is $C_1$–$C_4$ alkyl or phenyl optionally substituted with 1 or 2 $R_{3-2}$ where $R_{3-2}$ is —$CH_3$, —$OCH_3$, —F and —Cl;
where:
(C-I) $R_9$ is $R_{9-1}$:$R_{9-2}$ and $R_{11}$ is $R_{11-1}$:$R_{11-2}$, where one of $R_{9-1}$ and $R_{9-2}$ is —H and the other taken together with one of $R_{11-1}$ and $R_{11-2}$ to form a second bond between $C_9$ and $C_{11}$ and the other of $R_{11-1}$ and $R_{11-2}$ is —H;
(C-II) $R_9$ is —H;—H and $R_{11}$ is =O;
(C-III) $R_9$ is —H:—H and $R_{11}$ is $\alpha$-$R_{11-3}$:$\beta$-$R_{11-4}$ where one of $R_{11-3}$ and $R_{11-4}$ is —H or —OH and the other is —H;
(D-I) $R_{16}$ is $R_{16-1}$:$R_{16-2}$ and $R_{17}$ is $R_{17-1}$:$R_{17-2}$, where one of $R_{16-1}$ and $R_{16-2}$ is —H or —$CH_3$ and the other taken together with one of $R_{17-1}$ and $R_{17-2}$ forms a second bond between $C_{16}$ and $C_{17}$, and the other of $R_{17-1}$ and $R_{17-2}$ is —C(=Z)—($CH_2$)$_n$—$NR_{21A}R_{21B}$, where Z is =O, =$CH_2$ or $R_{20-1}$:—H where $R_{20-1}$ is —H or —$CH_3$, where n is 0 through 6, where
(A) $R_{21A}$ is
(1) —($CH_2$)$_m$—$NR_{21-1}$—heteroaryl, where m is 2, 3, or 4, where $R_{21-1}$ is —H or $C_1$–$C_3$ alkyl, where heteroaryl is:
(a) pyridin-2- (F-1), 3- (F-2) or 4-yl (F-3) or the N-oxide thereof optionally substituted by 1 or 2 $R_{21-2}$, being the same or different, where $R_{21-2}$ is
(i) —F,
(ii) —Cl,
(iii) —Br,
(iv) $C_1$–$C_5$ alkyl,
(v) —$CH_2$—CH=$CH_2$,
(vi) —aryl, where aryl is phenyl optionally substituted with 1 through 2 —F, —Cl, —Br, $C_1$–$C_3$ alkoxy, —COOH, —$NH_2$, $C_1$–$C_3$ alkylamino, di($C_1$–$C_3$)alkylamino, where the alkyl groups are the same or different, 1-pyrrolidinyl-, 1-piperidinyl, 1-hexamethylenimino—, 1-heptamethylenimino—, $C_2$–$C_4$ acylamino and —NH—CHO
(vii) —$NR_{21-3}R_{21-3}$ where the $R_{21-3}$s are the same or different and are —H, $C_1$–$C_3$ alkyl or —$CH_2$—CH=$CH_2$,
(viii$\alpha$) *$CH_2$—($CH_2$)$_q$—$CH_2$—N*— where the atoms marked with an asterisk (*) are bonded to each other resulting in the formation of a ring, where q is 1 through 5, (viii$\beta$) *$CH_2$—$CH_2$—($CH_2$)$_c$—G—($CH_2$)$_d$—$CH_2$—$CH_2$—N*— where the atoms marked with an asterisk (*) are bonded to each other resulting in the formation of a ring (F-4), where G is —O—, —S—, —SO—, —$SO_2$— or —$NHR_{21-4}$, where $R_{21-4}$ is —H, $C_1$–$C_3$ alkyl, or aryl as defined above, where c and d are the same or different and are 0 through 2 with the proviso that the total number of ring carbon atoms is 4, 5 or 6,
(ix) 3-pyrrolin-1-yl, (F-5)
(x) pyrrol-1-yl optionally substituted with $C_1$–$C_3$ alkyl, (F-6)
(xi) piperidin-1-yl optionally substituted with 1 or 2 $C_1$–$C_3$ alkyl, (F-7)
(xii) 1,2,3,6-tetrahydropyridin-1-yl, (F-8)
(xiii) 1-hexamethyleneimino containing a 3- or 4- double bond or 3- and 5- double bonds, (F-9)
(xiv) 1,4-dihydro-1-pyridinyl substituted in the 4 position by two $C_1$–$C_3$ alkyl being the same or different, (F-10)
(xv) —OH,
(xvi) $C_1$–$C_3$ alkoxy,
(xvii) —$NR_{21-7}$—($CH_2$)$_e$-Q where Q is 2-pyridinyl where $R_{21-7}$ is —H or $C_1$–$C_3$ alkyl and e is 0 through 3,
(xviii) pyridin-2-, 3- or 4-yl,
(xix) —$CF_3$
(xx) —$CCl_3$
(b) 1,3,5-triazin-2-yl or the N-oxide thereof optionally substituted at the 4- and/or 6- position with $R_{21-2}$ where $R_{21-2}$ is as defined above, (F-11)
(c) pyrimidin-4-yl or the N-oxide thereof optionally substituted at the 2- and/or 6- and 5- and/or 6- position with $R_{21-2}$ where $R_{21-2}$ is as defined above, (F-12)
(d) pyrimidin-2-yl optionally substituted at 4- and/or 6- position with 1 or 2 $R_{21-2}$ as defined above, (F-13)
(e) pyrazin-2-yl optionally substituted with 1 or 2 $R_{21-2}$ as is defined above, (F-14)
(f) imidazol-2-yl optionally substituted in the 1 position with $C_1$–$C_3$ alkyl or -aryl, where aryl is as defined above, and further optionally substituted with 1 or 2 $R_{21-2}$ as defined above, (F-15)
(g) 1,3,4-triazol-2-yl optionally substituted in the 1 position with $C_1$–$C_3$ alkyl or -aryl, where aryl is as defined above, and further optionally substituted with $R_{21-2}$ as defined above, (F-16)
(h) imidazol-4- or 5-yl optionally substituted in the 1 position with $C_1$–$C_3$ alkyl or -aryl, where aryl is as defined above, and further optionally substituted with 1 or 2 $R_{21-2}$ as defined above, (F-17)
(i) benzo[b]thien-2-yl, (F-18)
(j) indol-2-yl, (F-19)
(k) benzo[b]thiazol-2-yl, (F-20)
(l) benzimidazol-2-yl, (F-21)
(m) 4-[2-[4-[2,6-bis(1-pyrrolidinyl)-4-pyrimidinyl]-1-piperazinyl]ethyl]piperazinyl, (F-22)

(n) 1,2,4-triazin-3-yl optionally substituted at the 5- and/or 6- position with $R_{21-2}$ as is defined above, (F-23)

(2) (1-piperazinyl)-($C_2$-$C_4$)alkyl optionally substituted in the 4- position with -aryl or -heteroaryl as defined above, (F-24)

(3) -heteroaryl, as defined above, (4) —$(CH_2)_m$—$X_4$ where m is as defined above and where $X_4$ is (a) —O—$CH_2CH_2$—Y, where Y is $C_1$-$C_3$ alkylamino, di($C_1$-$C_3$)alkylamino where the alkyl groups are the same or different, $C_3$-$C_6$ alkyleneimino, optionally substituted with 1 or 2 $C_1$-$C_3$ alkyl, (b) —$NR_{21-5}CH_2CH_2$—Y, where $R_{21-5}$ is —H or $C_1$-$C_3$ alkyl and Y is as defined above, (c) —$(CH_2)_g$—N($R_{21-5}$)-heteroaryl, where g is 2, 3 or 4, and where $R_{21-5}$ and heteroaryl are as defined above, (6) —$(CHCH_3)_b$—$(CH_2)_f$—$R_{21-9}$, where b is 0 and f is 1 through 3 or b is one and f is 0 through 3, where $R_{21-9}$ is phenyl substituted with 1 through 3 —OH, $C_1$-$C_3$ alkoxy, —$NR_{21-10}R_{21-11}$ where $R_{21-10}$ and $R_{21-11}$ are the same or different and are —H, $C_1$-$C_3$ alkyl or are taken together with the attached nitrogen atom to form a $C_4$-$C_7$ cyclicamino ring, (7) -$(CH_2)_i$-heteroaryl, where i is 1 through 4 and heteroaryl is as defined above, (8) (1-piperazinyl)acetyl substituted in the 4- position by heteroaryl where heteroaryl is as defined above, (F-25)

(9) (1-piperazinyl)carbonylmethyl substituted in the 4- position by -heteroaryl where heteroaryl is as defined above, and (F-26)

(B) $R_{21B}$ is (1) —H, (2) $C_1$-$C_3$ alkyl, (3) $C_5$-$C_7$ cycloalkyl, (4) —$(CH_2)_m$—$NR_{21-1}$-heteroaryl, where m, $R_{21-1}$ and heteroaryl are as defined above, (5) (1-piperazinyl)-($C_2$-$C_4$)alkyl optionally substituted in the 4- position with -aryl or -heteroaryl as defined above, (F-24)

(6) —$(CH_2)_m$—$X_4$, where m and $X_4$ are as defined above, (7) —$(CH_2)_m$—$NR_{21-6}R_{21-8}$, where m, $R_{21-6}$ and $R_{21-8}$ are as defined above, (8) —$(CHCH_3)_b$—$(CH_2)_f$—$R_{21-9}$, where b, f and $R_{21-9}$ are as defined above, (C) $R_{21A}$ and $R_{21B}$ are taken together with the attached nitrogen atom to form a heterocyclic ring selected from the group consisting of (1) 2-(carboxy)-1-pyrrolidinyl optionally as the $C_1$-$C_3$ alkyl ester or as a pharmaceutically acceptable salt, (F-27)

(2) 2-(carboxy)-1-piperidinyl optionally as the $C_1$-$C_3$ alkyl ester or as a pharmaceutically acceptable salt, (F-28)

(3) 2-(carboxy)-1-hexamethyleneimino optionally as the $C_1$-$C_3$ alkyl ester or as a pharmaceutically acceptable salt, (F-29)

(4) 2-(carboxy)-1-heptamethyleneimino optionally as the $C_1$-$C_3$ alkyl ester or as a pharmaceutically acceptable salt, (F-30)

(5) 1-piperazinyl substituted in the 4- position with $R_{21-12}$—CO—$(CH_2)_j$— where $R_{21-12}$ is —heteroaryl, —$NR_{21-13}$heteroaryl and 2-furanyl, where $R_{21-13}$ is —H or $C_1$-$C_3$ alkyl, where j is 0 through 3 and aryl is as defined above, (F-31)

(6) 1-piperazinyl substituted in the 4- position with heteroaryl-$(CH_2)_j$-, where heteroaryl and j are as defined above, (F-32)

(7) 1-piperazinyl substituted in the 4- position with aryl-$(CH_2)_j$-, where aryl and j are as defined above, (F-33)

(8) 4-hydroxy-1-piperidinyl substituted in the 4- position with aryl as defined above, (F-34)

(9) 1-piperazinyl substituted in the 4- position with heteroaryl-$NR_{21-13}$-CO-$(CH_2)_i$-, where heteroaryl, $R_{21-13}$ and i are as defined above; (F-35)

(D-II) $R_{16}$ is $\alpha$-$R_{16-3}$:$\beta$-$R_{16-4}$ where one of $R_{16-3}$ and $R_{16-4}$ is —H and the other is —H, —F, —$CH_3$ or —OH, and $R_{17}$ is =CH—$(CH_2)_p$—$NR_{21A}R_{21B}$, where p is 1 or 2, where $R_{21A}$ and $R_{21B}$ are as defined above;

(D-III) $R_{16}$ is $\alpha$-$R_{16-5}$:$\beta$-$R_{16-6}$ and $R_{17}$ is $\alpha$-$R_{17-5}$:$\beta$-$R_{17-6}$, where $R_{16-5}$ is —H, —OH, —F or —$CH_3$ and $R_{16-6}$ is —H, —OH, —F, or —$CH_3$, with the proviso that at least one of $R_{16-5}$ and $R_{16-6}$ is —H, where $R_{17-5}$ is —H, —OH, —$CH_3$, —$CH_2CH_3$, $C_2$-$C_7$ alkanoyloxy or —O—CO—aryl, where aryl is as defined above, and $R_{17-6}$ is —C(=Z)—$(CH_2)_n$—$NR_{21A}R_{21B}$, where Z, n, $R_{21A}$ and $R_{21B}$ are as defined above;

(D-IV) the 16,17-acetonide of a compound where $R_{16-5}$ is —OH, $R_{16-6}$ is —H, $R_{17-5}$ is —OH and $R_{17-6}$ is —C(=Z)—$(CH_2)_n$—$NR_{21A}R_{21B}$, where Z, n, —$R_{21A}$ and $R_{21B}$ are as defined above;

(D-V) $R_{16}$ is $\alpha$-$R_{16-7}$:$\beta$-$R_{16-8}$ and $R_{17}$ is $\alpha$-C(=Z)—$(CH_2)_n$—N—$R_{21A}R_{21B}$:$\beta$-H where Z, n, $R_{21A}$ and $R_{21B}$ are as defined above, where $R_{16-7}$ is —H, —OH, —F or —$CH_3$ and $R_{16-8}$ is —H, —OH, —F, or —$CH_3$, with the proviso that at least one of $R_{16-5}$ and $R_{16-6}$ is —H and pharmaceutically acceptable salts thereof, and hydrates and solvates thereof.

2. An amino-9,10-secosteroid according to claim 1 where $R_{16}$ and $R_{17}$ are (D-II) $R_{16}$ is $\alpha$-$R_{16-3}$:$\beta$-$R_{16-4}$ where one of $R_{16-3}$ and $R_{16-4}$ is —H and the other is —H, —F, —$CH_3$ or —OH, and $R_{17}$ is =CH—$(CH_2)_p$—$NR_{21A}R_{21B}$;

(D-III) $R_{16}$ is $\alpha$-$R_{16-5}$:$\beta$-$R_{16-6}$ and $R_{17}$ is $\alpha$-$R_{17-5}$:$\beta$-$R_{17-6}$, where $R_{16-5}$ is —H, —OH, —F or —$CH_3$ and $R_{16-6}$ is —H, —OH, —F, or —$CH_3$, with the proviso that at least one of $R_{16-5}$ and $R_{16-6}$ is —H, where $R_{17-5}$ is —H, —OH, —$CH_3$, —$CH_2CH_3$, $C_2$-$C_7$ alkanoyloxy or —O—CO—aryl, and where $R_{17-6}$ is —C(=Z)—$(CH_2)_n$—$NR_{21A}R_{21B}$;

(D-IV) the 16,17-acetonide of a compound where $R_{16-5}$ is —OH, $R_{16-6}$ is —H, $R_{17-5}$ is —OH and $R_{17-6}$ is —C(=Z)—$(CH_2)_n$—$NR_{21A}R_{21B}$;

(D-V) $R_{16}$ is $\alpha$-$R_{16-7}$:$\beta$-$R_{16-8}$ and $R_{17}$ is $\alpha$-C(=Z)-$(CH_2)_n$—N—$R_{21A}R_{21B}$:$\beta$-H where $R_{16-7}$ is —H, —OH, —F or —$CH_3$ and $R_{16-8}$ is —H, —OH, —F, or —$CH_3$, with the proviso that at least one of $R_{16-5}$ and $R_{16-6}$ is —H.

3. An amino-9,10-secosteroid according to claim 1 where $R_{17}$ is $\alpha$-$R_{17-5}$:$\beta$-$R_{17-6}$, where $R_{17-5}$ is —H, —OH, —$CH_3$, —$CH_2CH_3$, $C_2$-$C_7$ alkanoyloxy or —O—CO—aryl, and where $R_{17-6}$ is —C(=Z)—$(CH_2)_n$—$NR_{21A}R_{21B}$.

4. An amino-9,10-secosteroid according to claim 1 where $R_{17}$ is =CH—$(CH_2)_p$—$NR_{21A}R_{21B}$.

5. An amino-9,10-secosteroid according to claim 1 where $R_{11}$ is =O.

6. An amino-9,10-secosteroid according to claim 1 where $R_9$ is $R_{9-1}:R_{9-2}$ and $R_{11}$ is $R_{11-2}$, where one of $R_{9-1}$ and $R_{9-2}$ is —H and the other taken together with one of $R_{11-1}$ and $R_{11-2}$ to form a second bond between $C_9$ and $C_{11}$ and the other of $R_{11-1}$ and $R_{11-2}$ is —H.

7. An amino-9,10-secosteroid according to claim 1 where $R_9$—H:—H and $R_{11}$ is $\alpha$-$R_{11-3}$:$\beta$-$R_{11-4}$ where one of $R_{11-3}$ and $R_{11-4}$ is —OH and the other is —H.

8. An amino-9,10-secosteroid according to claim 1 where n is 1.

9. An amino-9,10-secosteroid according to claim 1 where Z is =O.

10. An amino-9,10-secosteroid according to claim 1 where Z is —H:—H.

11. An amino-9,10-secosteroid according to claim 1 where $R_{21A}$ and $R_{21B}$ are taken together with the attached nitrogen atom form 1-piperazinyl substituted in the 4- position with -(CH$_2$)$_j$-heteroaryl.

12. An amino-9,10-secosteroid according to claim 1 where j is 0.

13. An amino-9,10-secosteroid according to claim 1 where $R_{21A}$ and $R_{21B}$ are taken together with the attached nitrogen atom form 1-piperazinyl substituted in the 4-position with -(CH$_2$)$_j$-heteroaryl where j is 0 and heteroaryl is selected from the group consisting of
  (a) 1,3,5-triazin-2-yl optionally substituted in the 4- and/or 6- position with $R_{21-2}$,
  (b) pyrimidin-2-yl optionally substituted at 4- and/or 6- position with 1 or 2 $R_{21-2}$,
  (c) pyrimidin-4-yl optionally substituted at the 2- and/or 6- position with $R_{21-2}$ and
  (d) pyridin-2-yl optionally substituted by 1 or 2 $R_{21-2}$, being the same of different.

14. An amino-9,10-secosteroid according to claim 13 where $R_{21A}$ and $R_{21B}$ are taken together with the attached nitrogen atom form 1-piperazinyl substituted in the 4-position with -(CH$_2$)$_j$-heteroaryl where j is 0 and heteroaryl is selected from the group consisting of
  (a) 1,3,5-triazin-2-yl substituted at the 4- and 6- position with pyrrolidine or diethylamine,
  (b) pyrimidin-2-yl optionally substituted at the 4- and 6- position with pyrrolidine,
  (c) pyrimidin-4-yl optionally substituted at the 2- and 6- position with pyrrolidine or diethylamine,
  (d) pyridin-2-yl and
  (e) pyridin-2-yl substituted with pyrrolidine, ethylamine or diethylamine.

15. An amino-9,10-secosteroid according to claim 1 where $R_{21A}$ and $R_{21B}$ are taken together with the attached nitrogen atom form a cyclic amine substituent selected from the group consisting of
4-(2-pyridinyl)-1-piperazinyl,
4-[4,6-bis(2-propenylamino)-1,3,5-triazin-2-yl]-1-piperazinyl,
4-[2,6-bis(1-pyrrolidinyl)-4-pyrimidinyl]-1-piperazinyl,
4-[2,6-bis(morpholino)-4-pyrimidinyl]-1-piperazinyl,
4-[4,6-bis(diethylamino)-2-pyrimidinyl]-1-piperazinyl,
4-[4,6-bis(1-pyrrolidinyl)-1,3,5-triazin-2-yl]-1-piperazinyl,
4-[3,6-bis(diethylamino)-2-pyridinyl]-1-piperazinyl,
4-[3-(ethylamino)-2-pyridinyl]-1-piperazinyl,
4-[6-(diethylamino)-2-pyridinyl]-1-piperazinyl,
4-[4,6-bis(2-pyridinyl)-1,3,5-triazin-2-yl]-1-piperazinyl and
4-[2,6-bis(2-pyridinyl)-4-pyrimidinyl]-1-piperazinyl.

16. An amino-9,10-secosteroid according to claim 1 which is
3a-methyl-3α-hydroxy-7-[2-(5-hydroxy-2-methylphenyl)-ethyl]-3-[2-[4-(2,6-bis(1-pyrrolidinyl)-4-pyrimidinyl)-1-piperazinyl]acetyl]-octahydro-5H-inden-5-one,
3a-methyl-3α-hydroxy-7-(5-hydroxy-2-methylphenyl)-ethyl]-3-[2-[4-(2-pyridinyl)-1-piperazinyl]acetyl]octahydro-5H-inden-5-one,
3a-methyl-3α-hydroxy-7-[2-(5-hydroxy-2-methylphenyl)-ethyl]-3-[2-[4-[3-(ethylamino)-2-pyridinyl]-1-piperazinyl]acetyl]-octahydro-5H-inden-5-one,
3a-methyl-7-[2-(5-hydroxy-2-methylphenyl)-ethyl]-3-[2-[4-(2,6-bis(1-pyrrolidinyl)-4-pyrimidinyl)-1-piperazinyl]ethyl]-3α-octahydro-5H-inden-5-one,
3a-methyl-7-[2-(5-hydroxy-2-methylphenyl)-ethyl]-3-[2-[4-[3-(ethylamino)-2-pyridinyl]-1-piperazinyl]ethyl]-3α-octahydro-5H-inden-5-one,
3a-Methyl-3α-hydroxy-7-[2-(5-hydroxy-2-methylphenyl)-ethyl]-3-[2-[4-[2,6-bis(2-pyridinyl)-4-pyrimidinyl]-1-piperazinyl]acetyl]octahydro-5H-inden-5-one,
3a-methyl-7-[2-(5-hydroxy-2-methylphenyl)-ethyl]-3-[2-[4-[3-(ethylamino)-2-pyridinyl]-1-piperazinyl]ethylidene]-3α-octahydro-5H-inden-5-one,
3a-methyl-7-[2-(5-hydroxy-2-methylphenyl)-ethyl]-3-[2-[4-[3-(ethylamino)-2-pyridinyl]-1-piperazinyl]acetyl]-3α-octahydro-5H-inden-5-one,
3a-methyl-7-[2-(5-hydroxy-2-methylphenyl)-ethyl]-3-[2-[4-(2,6-bis(1-pyrrolidinyl)-4-pyrimidinyl)-1-piperazinyl]ethyl]-3α-octahydro-5H-inden-5-one,
3a-methyl-7-[2-(5-hydroxy-2-methylphenyl)ethyl]-3α-[2-[4-(2,6-bis(1-pyrrolidinyl)-4-pyrimidinyl)-1-piperazinyl]acetyl]-3β-octahydro-5H-inden-5-one,
3a-methyl-7-[2-(5-hydroxy-2-methylphenyl)ethyl]-3α-[2-[4-[3-(ethylamino) -2-pyridinyl]-1-piperazinyl]acetyl]-3β-octahydro-5H-inden-5-one,
3a-methyl-3β-[2-[4-[3,6-bis(diethylamino)-2-pyridinyl]-1-piperazinyl]acetyl]-7 -[2-(5-hydroxy-2-methylphenyl)ethyl]-3α-octahydro-5H-inden-5-one,
7a-methyl-1β-[2-[4-[3-(ethylamino)-2-pyridinyl]-1-piperazinyl]acetyl]-4α-[2-(5-hydroxy-2-methylphenyl)-ethyl]-2, 3, 3aα, 4, 7, 7a-hexahydro-Δ$^5$-1H-indene,
7a-methyl-4α-[2-(5-hydroxy-2-methylphenyl)-ethyl]-1β-[2-[4-(2,6-bis(1-pyrrolidinyl)-4-pyrimidinyl)-1-piperazinyl]acetyl]-2, 3, 3aα, 4, 7, 7a-hexahydro-Δ$^5$-1H-indene.

17. An amino-9,10-secosteroid according to claim 1 where $R_{21A}$ and $R_{21B}$ are taken together with the attached nitrogen atom form 1-piperazinyl substituted in the 4- position with -(CH$_2$)$_j$-aryl.

18. An amino-9,10-secosteroid according to claim 1 where the pharmaceutically acceptable salt is selected from the group consisting of hydrochloride, hydrobromide, hydrogen iodide, sulfate, phosphate, acetate, lactate, citrate, succinate, benzoate, salicyclate, pamoate, cyclohexanesulfamate, methanesulfonate, naphthalenesulfonate, p-toluenesulfonate, maleate, fumarate and oxalate.

* * * * *